(12) United States Patent
Chandran et al.

(10) Patent No.: US 10,842,802 B2
(45) Date of Patent: Nov. 24, 2020

(54) CONTROLLED RELEASE PHARMACEUTICAL DOSAGE FORMS

(71) Applicant: Medicis Pharmaceutical Corporation, Scottsdale, AZ (US)

(72) Inventors: Sajeev Chandran, Pune (IN); Shirishkumar Kulkarni, Pune (IN); Pravin Meghrajji Bhutada, Pune (IN); Ashish Ashokrao Deshmukh, Pune (IN); Douglas Bakan, Scottsdale, AZ (US); Mitchell Wortzman, Scottsdale, AZ (US)

(73) Assignee: MEDICIS PHARMACEUTICAL CORPORATION, Scottsdale, AZ (US)

( * ) Notice: Subject to any disclaimer, the term of this patent is extended or adjusted under 35 U.S.C. 154(b) by 553 days.

(21) Appl. No.: 13/890,173

(22) Filed: May 8, 2013

(65) Prior Publication Data
US 2014/0274970 A1 Sep. 18, 2014

(30) Foreign Application Priority Data

Mar. 15, 2013 (IN) .......................... 0304/KOL/2013

(51) Int. Cl.
A61K 31/65 (2006.01)
A61K 9/24 (2006.01)
A61K 9/00 (2006.01)
A61K 9/20 (2006.01)

(52) U.S. Cl.
CPC ............ A61K 31/65 (2013.01); A61K 9/0065 (2013.01); A61K 9/209 (2013.01); A61K 9/2086 (2013.01)

(58) Field of Classification Search
None
See application file for complete search history.

(56) References Cited

U.S. PATENT DOCUMENTS

| | | | |
|---|---|---|---|
| 4,952,402 | A | 8/1990 | Sparks et al. |
| 5,000,886 | A | 3/1991 | Lawter et al. |
| 5,051,262 | A | 9/1991 | Panoz et al. |
| 5,122,519 | A | 6/1992 | Ritter |
| 5,354,556 | A | 10/1994 | Sparks et al. |
| 5,516,531 | A | 5/1996 | Makino et al. |
| 5,538,954 | A | 7/1996 | Koch et al. |
| 5,780,055 | A | 7/1998 | Habib et al. |
| 5,789,395 | A | 8/1998 | Amin et al. |

(Continued)

FOREIGN PATENT DOCUMENTS

| | | |
|---|---|---|
| JP | 1994-024959 | 2/1994 |
| JP | 1997-95440 | 4/1997 |

(Continued)

OTHER PUBLICATIONS

Co-pending U.S. Appl. No. 13/536,052 inventors Bakan, D.A., et al., filed on June 28, 2012 (Filed With Request For Non-Publication).

(Continued)

Primary Examiner — Savitha M Rao
Assistant Examiner — Andrew P Lee
(74) Attorney, Agent, or Firm — Andrew J. Anderson, Esq.; Harter Secrest & Emery LLP

(57) ABSTRACT

The present disclosure provides novel controlled release pharmaceutical dosage form, methods of making the same, and methods of using the same to treat dermatological conditions.

20 Claims, 10 Drawing Sheets

(56) References Cited

U.S. PATENT DOCUMENTS

| | | |
|---|---|---|
| 5,919,775 A | 7/1999 | Amin et al. |
| 6,080,426 A | 6/2000 | Amey et al. |
| 6,077,533 A | 7/2000 | Oshlack et al. |
| 6,193,994 B1 | 2/2001 | Lee et al. |
| 6,245,350 B1 | 6/2001 | Amey et al. |
| 6,340,475 B2 | 1/2002 | Shell et al. |
| 6,497,901 B1 | 12/2002 | Royer |
| 6,635,280 B2 | 10/2003 | Shell et al. |
| 6,638,532 B2 | 10/2003 | Rudnic et al. |
| 6,730,320 B2 | 5/2004 | Rudnic et al. |
| 6,958,161 B2 | 10/2005 | Hayes et al. |
| 7,008,631 B2 | 3/2006 | Ashley |
| 7,014,858 B2 | 3/2006 | Ashley |
| 7,201,923 B1 | 4/2007 | van Lengerich |
| 7,211,267 B2 | 5/2007 | Ashley |
| 7,232,572 B2 | 6/2007 | Ashley |
| 7,485,319 B2 | 2/2009 | deVries et al. |
| 7,749,532 B2 | 7/2010 | Chang et al. |
| 7,910,128 B2 | 3/2011 | Chang et al. |
| 7,939,570 B2 | 5/2011 | Raul et al. |
| 7,951,398 B2 | 5/2011 | Dietrich et al. |
| 7,951,403 B2 | 5/2011 | Friesen et al. |
| 7,976,870 B2 | 7/2011 | Berner et al. |
| 7,976,871 B2 | 7/2011 | Vaya et al. |
| 8,052,983 B2 | 11/2011 | Ashley |
| 8,071,075 B2 | 12/2011 | Reed et al. |
| 8,088,726 B2 | 1/2012 | Yamamoto et al. |
| 8,114,062 B2 | 2/2012 | Muni et al. |
| 8,114,385 B2 | 2/2012 | Tamarkin et al. |
| 8,133,510 B2 | 3/2012 | Bartholomaeus et al. |
| 8,137,684 B2 | 3/2012 | Desai et al. |
| 8,192,749 B2 | 6/2012 | Ashley |
| 8,202,912 B2 | 6/2012 | Curatolo et al. |
| 8,206,740 B2 | 6/2012 | Chang et al. |
| 8,652,516 B1 | 2/2014 | Etchegaray et al. |
| 2002/0044968 A1 | 4/2002 | van Lengerich |
| 2003/0077297 A1 | 4/2003 | Chen et al. |
| 2003/0077301 A1 | 4/2003 | Maibach et al. |
| 2003/0091630 A1 | 5/2003 | Louie-Helm et al. |
| 2003/0104052 A1 | 6/2003 | Berner et al. |
| 2003/0130240 A1 | 7/2003 | Ashley |
| 2003/0133985 A1 | 7/2003 | Louie-Helm et al. |
| 2003/0180362 A1 | 9/2003 | Park et al. |
| 2003/0199480 A1 | 10/2003 | Hayes et al. |
| 2003/0211156 A1 | 11/2003 | Dansereau et al. |
| 2004/0022849 A1 | 2/2004 | Castan et al. |
| 2004/0115261 A1 | 6/2004 | Ashley |
| 2004/0147492 A1 | 7/2004 | Ashley |
| 2004/0185097 A1 | 9/2004 | Kannan et al. |
| 2004/0185105 A1 | 9/2004 | Berner et al. |
| 2004/0228915 A1 | 11/2004 | Noack et al. |
| 2005/0037071 A1 | 2/2005 | Cao et al. |
| 2005/0049210 A1 | 3/2005 | Murthy et al. |
| 2005/0152975 A1 | 7/2005 | Nakagami et al. |
| 2005/0266077 A1 | 12/2005 | Royer |
| 2006/0018933 A1 | 1/2006 | Vaya et al. |
| 2006/0057073 A1 | 3/2006 | Lintz |
| 2006/0147491 A1 | 7/2006 | DeWitt et al. |
| 2007/0141096 A1 | 6/2007 | Van Lengerich |
| 2007/0148235 A1 | 6/2007 | Nakagami et al. |
| 2008/0014257 A1 | 1/2008 | He et al. |
| 2008/0070873 A1 | 3/2008 | Alekshun et al. |
| 2008/0161273 A1 | 7/2008 | Arsonnaud et al. |
| 2008/0200533 A1 | 8/2008 | Krishnan |
| 2008/0233206 A1 | 9/2008 | Chomczynski |
| 2008/0248107 A1 | 10/2008 | Pilgaonkar et al. |
| 2008/0268045 A1 | 10/2008 | Dervieux et al. |
| 2008/0312168 A1 | 12/2008 | Pilgaonkar et al. |
| 2008/0312193 A1 | 12/2008 | Asscfa et al. |
| 2008/0318910 A1* | 12/2008 | Desjardins et al. .......... 514/152 |
| 2009/0011006 A1 | 1/2009 | Chang et al. |
| 2009/0053310 A1 | 2/2009 | Pilgaonkar et al. |
| 2009/0110728 A1 | 4/2009 | Rastogi et al. |
| 2009/0136568 A1 | 5/2009 | Lukas |
| 2009/0220611 A1 | 9/2009 | Dargelas et al. |
| 2009/0220613 A1 | 9/2009 | Odidi et al. |
| 2010/0184714 A1 | 7/2010 | Raul et al. |
| 2010/0215744 A1 | 8/2010 | Watt et al. |
| 2010/0291191 A1 | 11/2010 | Shoichet et al. |
| 2010/0291201 A1 | 11/2010 | Shah et al. |
| 2010/0305309 A1 | 12/2010 | Ho et al. |
| 2010/0330131 A1 | 12/2010 | Wortzman et al. |
| 2010/0330180 A1 | 12/2010 | Lukas |
| 2011/0027389 A1 | 2/2011 | Dunn |
| 2011/0052682 A1 | 3/2011 | Fatmi et al. |
| 2011/0104206 A1 | 5/2011 | Nanduri et al. |
| 2011/0117184 A1 | 5/2011 | Bromley et al. |
| 2011/0117197 A1 | 5/2011 | Emanuel et al. |
| 2011/0152212 A1 | 6/2011 | Crowther et al. |
| 2011/0159049 A1 | 6/2011 | Nakagami et al. |
| 2011/0171299 A1 | 7/2011 | deVries et al. |
| 2011/0171308 A1 | 7/2011 | Zhang et al. |
| 2011/0177165 A1 | 7/2011 | Gerber et al. |
| 2011/0212156 A1 | 9/2011 | Chang et al. |
| 2011/0223203 A1 | 9/2011 | Berkland et al. |
| 2011/0229569 A1 | 9/2011 | Pilgaonkar et al. |
| 2011/0244043 A1 | 10/2011 | Xu et al. |
| 2011/0262542 A1 | 10/2011 | Ashley |
| 2011/0264028 A1 | 10/2011 | Ramdas et al. |
| 2011/0268666 A1 | 11/2011 | Friedman et al. |
| 2011/0268807 A1 | 11/2011 | Su et al. |
| 2011/0287094 A1 | 11/2011 | Penhasi et al. |
| 2011/0288056 A1 | 11/2011 | Chang et al. |
| 2011/0294902 A1 | 12/2011 | Curatolo et al. |
| 2011/0301129 A1 | 12/2011 | Berner et al. |
| 2011/0305643 A1 | 12/2011 | Gurge et al. |
| 2011/0319368 A1 | 12/2011 | Chang et al. |
| 2012/0009290 A1 | 1/2012 | Segond et al. |
| 2012/0021009 A1* | 1/2012 | Prinderre et al. ............. 424/400 |
| 2012/0028929 A1 | 2/2012 | Power et al. |
| 2012/0035121 A1 | 2/2012 | Rudnic et al. |
| 2012/0039969 A1 | 2/2012 | Bar-Shalom et al. |
| 2012/0045486 A1 | 2/2012 | Bravo Cordero et al. |
| 2012/0045504 A1 | 2/2012 | Whitehead et al. |
| 2012/0076766 A1 | 3/2012 | Phillips et al. |
| 2012/0100214 A1 | 4/2012 | Segura et al. |
| 2012/0108552 A1 | 5/2012 | Ashley |

FOREIGN PATENT DOCUMENTS

| | | |
|---|---|---|
| JP | 2004-502723 A | 1/2004 |
| JP | 2004-525955 A | 8/2004 |
| JP | 2006-522162 A | 9/2006 |
| JP | 2006-523703 A | 10/2006 |
| WO | WO 95/031972 A1 | 11/1995 |
| WO | WO 98/009597 A2 | 3/1998 |
| WO | WO 98/056360 A2 | 12/1998 |
| WO | WO 00/021504 A1 | 4/2000 |
| WO | WO 02/047607 A2 | 6/2002 |
| WO | WO 02/083106 A1 | 10/2002 |
| WO | WO 03/035029 A1 | 5/2003 |
| WO | WO 03/035041 A1 | 5/2003 |
| WO | WO 03/063834 A1 | 8/2003 |
| WO | WO 03/075852 A2 | 9/2003 |
| WO | WO 03/086344 A1 | 10/2003 |
| WO | WO 03/086366 A1 | 10/2003 |
| WO | WO 2004/000276 A1 | 12/2003 |
| WO | WO 2004/000360 A1 | 12/2003 |
| WO | WO 2004/041253 A1 | 5/2004 |
| WO | WO 2004/062577 A2 | 7/2004 |
| WO | WO 2004/066910 A2 | 8/2004 |
| WO | WO 2004/087175 A1 | 10/2004 |
| WO | WO 2004/091483 A2 | 10/2004 |
| WO | 2004-096125 A2 | 11/2004 |
| WO | WO 2004/112713 A2 | 12/2004 |
| WO | WO 2005/011707 A1 | 2/2005 |
| WO | WO 2005/016311 A1 | 2/2005 |
| WO | WO 2005/025488 A2 | 3/2005 |
| WO | WO 2005/046651 A1 | 5/2005 |
| WO | WO 2007/004236 A1 | 1/2007 |
| WO | WO 2007/036671 A2 | 4/2007 |
| WO | WO 2007/036952 A2 | 4/2007 |
| WO | WO 2007/038867 A1 | 4/2007 |
| WO | WO 2007/052289 A2 | 5/2007 |

(56) References Cited

FOREIGN PATENT DOCUMENTS

| WO | WO 2007/087416 A2 | 8/2007 |
|----|----|----|
| WO | WO 2007/112581 A1 | 10/2007 |
| WO | WO 2008/001341 A1 | 1/2008 |
| WO | WO 2008/104996 A2 | 9/2008 |
| WO | WO 2009/150514 A1 | 12/2009 |
| WO | WO 2010/033800 A2 | 3/2010 |
| WO | WO 2010/035273 A2 | 4/2010 |
| WO | WO 2010/038234 A1 | 4/2010 |
| WO | WO 2010/038237 A2 | 4/2010 |
| WO | WO 2010/075065 A2 | 7/2010 |
| WO | WO 2010/132819 A1 | 11/2010 |
| WO | WO 2010/138837 A2 | 12/2010 |
| WO | WO 2011/044208 A1 | 4/2011 |

OTHER PUBLICATIONS

Non-Final Rejection, dated Jan. 13, 2014, for U.S. Appl. No. 13/536,052, filed Jun. 28, 2012 (Application filed with request for non-publication).

Agwuh, K.N. and Macgowan, A., "Pharmacokinetics and pharmacodynamics of the tetracyclines including glycylcyclines," *Journal of Antimicrobial Chemotherapy* 58:256-265, Oxford University Press, England (2006).

Saivin, S. and Houin, G., "Clinical Pharmacokinetics of Doxycycline and Minocycline," *Clinical Pharmacokinetics* 15:355-366, ADIS Press Limited, Germany (1988).

JPO Office Action from corresponding Japanese Patent Application No. 2016-500595 dated Dec. 26, 2017 with translation (10 pages).

\* cited by examiner

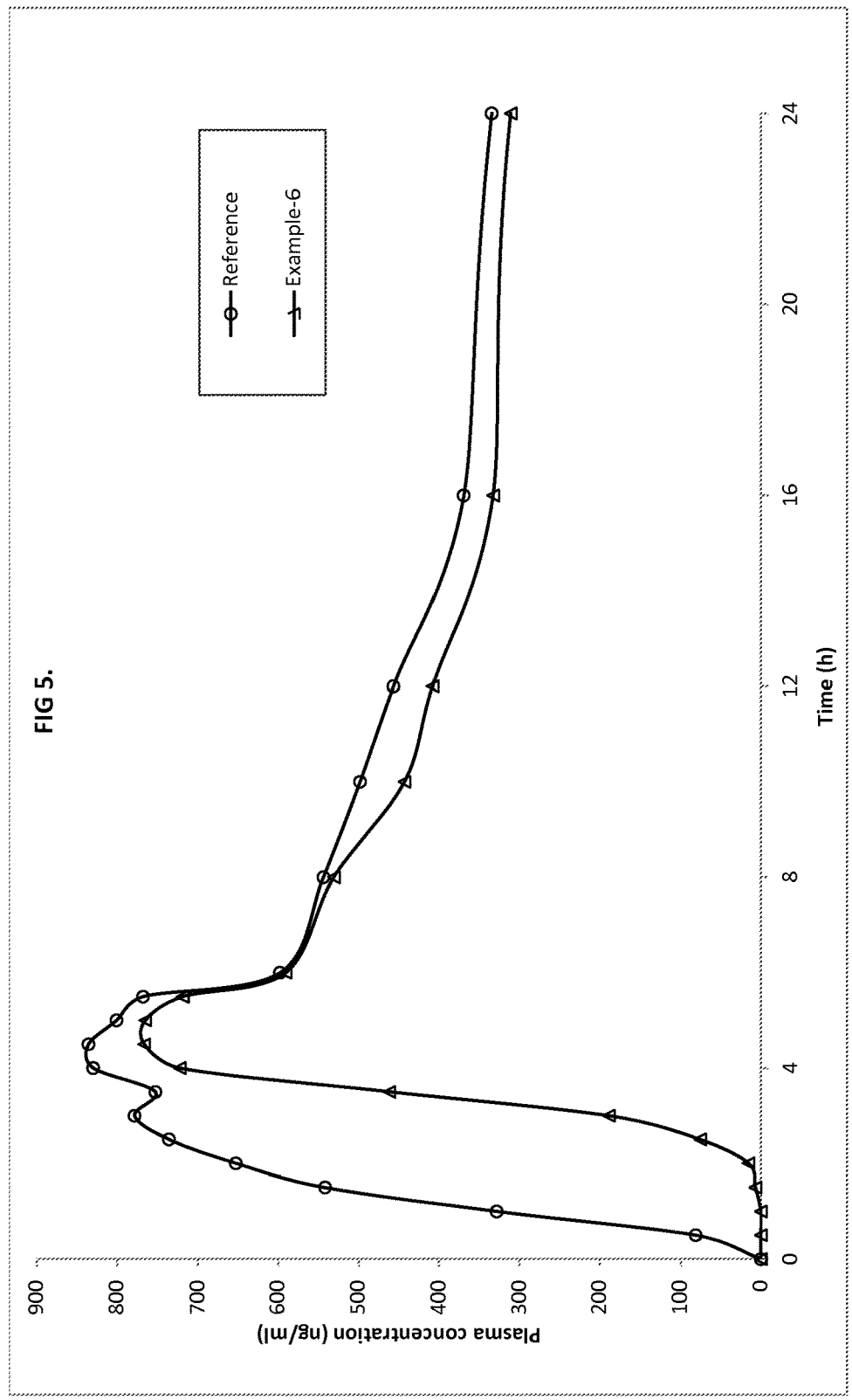

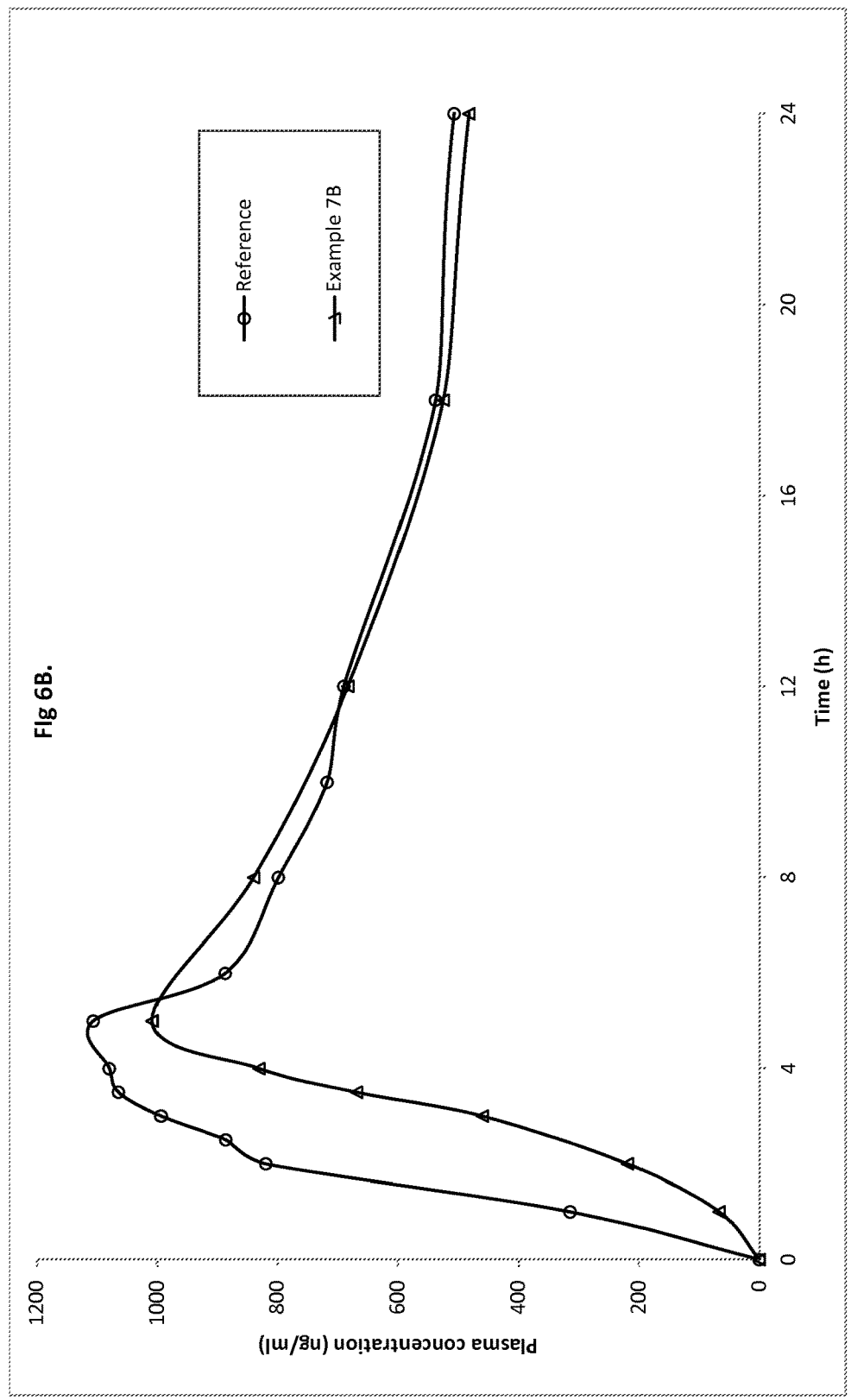

CONTROLLED RELEASE PHARMACEUTICAL DOSAGE FORMS

FIELD

This application relates to pharmaceutical dosage forms.

BACKGROUND

The tetracycline class of compounds are known in the art to be useful for the treatment of certain dermatological conditions. For example, MONODOX®, an immediate release doxycycline monohydrate dosage form, can be used as an adjunctive therapy for the treatment of severe acne. Similarly, DORYX®, a doxycycline hyclate delayed release tablet, can also be used as an adjunctive therapy for the treatment of severe acne. And, while the mechanism of action has not been completely elucidated, doxycycline in the form of ORACEA® has been shown to be efficacious for the treatment of the papules and pustules associated with rosacea.

Minocycline dosage forms have also been shown to be suitable for treating dermatological conditions. In particular, SOLODYN®, a controlled release minocycline dosage form, has been shown to be efficacious for the treatment of moderate to severe acne.

SUMMARY

The present disclosure provides a doxycycline formulation that is retained and released in a controlled manner in the upper portion of the gastrointestinal tract. The formulation provides enhanced efficacy and reduced side effects and/or adverse effects when compared to conventional immediate release dosage forms of doxycycline. Although delaying the release of doxycycline has previously been reported to decrease doxycycline's oral bioavailability, it has now been surprisingly found that when administered in a controlled release fashion, the relative oral bioavailability when compared to immediate release formulation of doxycycline was more than about 80% and in certain embodiments, more than about 90% orally bioavailable.

In certain embodiments, the present disclosure provides a controlled release pharmaceutical dosage form comprising a therapeutically effective amount of doxycycline, one or more bioadhesive/mucoadhesive agents, one or more release controlling agents, and pharmaceutically acceptable excipients.

In certain embodiments, the present disclosure provides a controlled release pharmaceutical dosage form, which comprises a therapeutically effective amount of doxycycline, one or more release controlling agents, and one or more pharmaceutically acceptable excipients, wherein the dosage form is formulated to increase and/or control the residence time of the dosage form in the gastrointestinal tract.

In certain embodiments, the present disclosure provides a controlled release pharmaceutical dosage form, which comprises a therapeutically effective amount of doxycycline, one or more bioadhesive polymers, and one or more pharmaceutically acceptable excipients, wherein the dosage form is formulated to increase and/or control the residence time of the dosage form in the gastrointestinal tract.

In certain embodiments, the present disclosure provides a controlled release pharmaceutical dosage form in the form of a multilayer tablet comprising a) a first layer comprising a therapeutically effective amount of doxycycline and one or more pharmaceutically acceptable excipients wherein the first layer provides an immediate release and/or controlled release of doxycycline; b) at least a second layer comprising doxycycline and one or more polymers wherein the second layer provides increased residence time of the dosage form in the upper portion of the gastrointestinal tract; and, optionally, c) a coating layer on the multilayer tablet.

In certain embodiments, the present disclosure provides a controlled release pharmaceutical dosage form in the form of a multilayer tablet comprising a) a first layer which comprises a first therapeutically effective amount of doxycycline and one or more pharmaceutically acceptable excipients wherein the first layer provides an immediate release and/or controlled release of doxycycline; b) at least a second layer which comprises doxycycline and one or more polymers wherein the second layer provides increased residence time of the dosage form in the upper portion of the gastrointestinal tract; c) a first coating over the multilayer tablet; and d) a second coating over the first coating, wherein the second coating contains a second therapeutically effective amount of doxycycline. In certain embodiments, the first coating is an enteric coating. In certain embodiments, the second coating provides for an immediate release of the second therapeutically effective amount of doxycycline.

In certain embodiments, the present disclosure provides a controlled release pharmaceutical dosage form in the form of a multilayer tablet comprising a) a first layer which comprises a first therapeutically effective amount of doxycycline and one or more pharmaceutically acceptable excipients, wherein the first layer provides a controlled release of the first therapeutically effective amount of doxycycline; b) a second layer which comprises a second therapeutically effective amount of doxycycline and one or more pharmaceutically acceptable excipients, wherein said second layer provides immediate release of the second therapeutically effective amount of doxycycline; and c) a third layer which comprises a bioadhesive agent and optionally one or more pharmaceutically acceptable excipients, wherein the third layer provides increased residence time of the dosage form in the gastrointestinal tract by virtue of its bioadhesive properties.

In certain embodiments, the present disclosure provides a controlled release pharmaceutical dosage form in the form of a multilayer tablet comprising a) a first layer comprising a first therapeutically effective amount of doxycycline and one or more pharmaceutically acceptable excipients, wherein the first layer provides a controlled release of doxycycline; and b) a second layer comprising a bioadhesive agent, wherein said bioadhesive agent provides increased residence time of the dosage form in the upper portion of the gastrointestinal tract. In certain embodiments, the second layer comprising a bioadhesive layer can optionally contain a second amount of doxycycline.

In certain embodiments, the present disclosure provides a method for treating acne, rosacea, or a combination thereof comprising administering to a patient in need thereof a controlled release pharmaceutical dosage form comprising doxycycline, wherein said controlled release pharmaceutical dosage form has a mean $C_{max}$ that is at least about 70% that of an immediate release dosage form of equivalent strength and has an AUC that is at least about 85% of an immediate release dosage form of equivalent strength.

In certain embodiments the controlled release dosage form has an AUC that is at least about 90% that of the immediate release dosage form of equivalent strength. In other embodiments, the controlled release dosage form has an AUC that is at least about 95% that of the immediate release dosage form of equivalent strength. In still other embodiments, the controlled release dosage form has an AUC that is at least about 97% that of the immediate release dosage form of equivalent strength. In yet another embodiment, the controlled release dosage form has an AUC that is at least about 99% that of the immediate release dosage form of equivalent strength.

In certain embodiments, the controlled release pharmaceutical dosage form has a mean $C_{max}$ that is at least about 80% that of an immediate release dosage form of equivalent strength.

In some embodiments, the controlled release pharmaceutical dosage form has a mean $C_{max}$ that is at least about 90% that of an immediate release dosage form of equivalent strength.

In other embodiments, the controlled release pharmaceutical dosage form has a mean $C_{max}$ that is at least about 95% that of an immediate release dosage form of equivalent strength.

In still other embodiments, the controlled release pharmaceutical dosage form has a mean $C_{max}$ that is at least about 98% that of an immediate release dosage form of equivalent strength.

In yet another embodiment, the controlled release pharmaceutical dosage form has a mean $C_{max}$ that is at least about 100% that of an immediate release dosage form of equivalent strength.

In still another embodiment, the controlled release pharmaceutical dosage form has a mean $C_{max}$ that is at least about 105% that of an immediate release dosage form of equivalent strength.

In another embodiments, the present disclosure provides a method for treating acne, rosacea, or a combination thereof comprising administering to a patient in need thereof a controlled release dosage form comprising doxycycline, wherein said dosage form has a $t_{max}$ that is at least about 1.15 times greater than the $t_{max}$ of an immediate release dosage form of equivalent strength.

In another embodiments, the dosage form has a $t_{max}$ that is at least about 1.2 times greater than the $t_{max}$ of an immediate release dosage form of equivalent strength.

In yet another embodiments, the dosage form has a $t_{max}$ that is at least about 1.5 times greater than the $t_{max}$ of an immediate release dosage form of equivalent strength.

In still another embodiment, the dosage form has a $t_{max}$ that is at least about 1.7 times greater than the $t_{max}$ of an immediate release dosage form of equivalent strength.

The present disclosure further provides a method of treating acne, rosacea, or a combination thereof comprising administering to a patient in need thereof, a controlled release pharmaceutical dosage form comprising doxycycline, wherein the dosage form has an in vitro dissolution profile, such that at least about 10% to 25% of the total doxycycline present in the dosage form is released in 1 hour, or at least about 25% to 50% of the total doxycycline is released in 4 hours, or at least about more than 90% of the total doxycycline is released in 10 hours, wherein the release profile is measured in a USP Basket apparatus using 0.1N HCl at 100 rpm.

In yet another embodiment, the present disclosure provides a method of treating acne, rosacea, or a combination thereof comprising administering to a patient in need thereof a controlled release pharmaceutical dosage form comprising a controlled release doxycycline layer, a swellable and/or floating layer, an expandable porous coating, optionally a seal coating, and an immediate release doxycycline overcoat.

In certain embodiments, the controlled release doxycycline layer can include a first amount of doxycycline and the immediate release doxycycline layer can include a second amount of doxycycline.

In some embodiments, the first amount of doxycycline is from about 5 to about 15 weight % doxycycline based on the total weight of the dosage form.

In some embodiments, the second amount of doxycycline is from about 0.5 to about 3.2 weight % doxycycline based on the total weight of the dosage form.

The present disclosure further provides a method of treating acne, rosacea, or a combination thereof comprising administering to a patient in need there of a controlled release pharmaceutical dosage form comprising a swellable controlled release drug core, a permeable/expandable porous coating, and an immediate release doxycycline overcoat.

In some embodiments, the swellable controlled release drug core comprises from about 5 to about 15 weight % doxycycline based on the total weight of the dosage form.

In some embodiments, the immediate release doxycycline overcoat comprises from about 0.5 to about 3.2 weight % doxycycline based on the total weight of the dosage form.

The present disclosure further provides a method of treating acne, rosacea, or a combination thereof comprising administering to a patient in need thereof a controlled release pharmaceutical dosage form comprising a controlled release layer, an inert swellable/bioadhesive layer, and an immediate release doxycycline overcoat.

In some embodiments, the controlled release layer comprises from about 5 to about 15 weight % doxycycline based on the total weight of the dosage form.

In some embodiments, the immediate release doxycycline overcoat comprises from about 0.5 to about 3.2 weight % doxycycline based on the total weight of the dosage form.

In yet another embodiment, the present disclosure provides a method of treating acne, rosacea, or a combination thereof comprising administering to a patient in need thereof, a controlled release pharmaceutical dosage form comprising doxycycline and having a mean $C_{max}$ in the range of about 400 to about 1400 ng/ml measured after oral administration to a patient in a fed state.

In still another embodiment, the present disclosure provides a method of treating acne, rosacea, or a combination thereof comprising administering to a patient in need thereof, a controlled release pharmaceutical dosage form comprising doxycycline and having an area under the plasma concentration versus time curve selected from the group consisting of from about 13,000 to about 21,000 ng/ml/h (0-48 hours), from about 15,000 to about 19,000 ng/ml/h (0-48 hours), about 23,000 to about 37,000 ng/ml/h (0-96 hours), and about 26,000 to about 33,000 ng/ml/h (0-96 hours), each as measured after oral administration of a single dose of the dosage form to a patient in a fed state.

In yet another embodiment, the present disclosure provides a controlled release pharmaceutical dosage form comprising a controlled release doxycycline layer, a swellable and/or floating layer, an expandable porous coating, optionally a seal coating, and an immediate release doxycycline overcoat.

In some embodiments, the controlled release doxycycline layer can include a first amount of doxycycline and the immediate release doxycycline layer can include a second amount of doxycycline.

In some embodiments, the first amount of doxycycline is from about 5 to about 15 weight % doxycycline based on the total weight of the dosage form.

In some embodiments, the second amount of doxycycline is from about 0.5 to about 3.2 weight % doxycycline based on the total weight of the dosage form.

In yet another embodiment, the present disclosure provides a controlled release pharmaceutical dosage form comprising a swellable controlled release drug core, a permeable/expandable porous coating, an optional seal coating, and an immediate release doxycycline overcoat.

In some embodiments, the swellable controlled release drug core comprises from about 5 to about 15 weight % doxycycline based on the total weight of the dosage form.

In some embodiments, the immediate release doxycycline overcoat comprises from about 0.5 to about 3.2 weight % doxycycline based on the total weight of the dosage form.

In yet another embodiment, the present disclosure provides a controlled release pharmaceutical dosage form comprising a controlled release layer, an inert swellable/bioadhesive layer, and an immediate release doxycycline overcoat.

In some embodiments, the controlled release layer comprises from about 5 to about 15 weight % doxycycline based on the total weight of the dosage form.

In some embodiments, the immediate release doxycycline overcoat comprises from about 0.5 to about 3.2 weight % doxycycline based on the total weight of the dosage form.

In some embodiments, the present disclosure provides a controlled release pharmaceutical dosage form comprising doxycycline having a mean $C_{max}$ in the range of about 400 to about 1400 ng/ml measured after oral administration to a patient in a fed state.

In yet another embodiment, the present disclosure provides a controlled release pharmaceutical dosage form comprising doxycycline having an area under the plasma concentration veruss time curve selected from the group consisting of from about 13,000 to about 21,000 ng/ml/h (0-48 hours), from about 15,000 to about 19,000 ng/ml/h (0-48 hours), about 23,000 to about 37,000 ng/ml/h (0-96 hours), and about 26,000 to about 33,000 ng/ml/h (0-96 hours), each as measured after oral administration of a single dose of the dosage form to a patient in a fed state.

It should be understood that the above summary is not intended to describe every embodiment or every implementation of the various formulations disclosed herein. The Detailed Description, Figures, and Examples sections further exemplify illustrative embodiments. The various embodiments described herein are intended to be disclosed in combinations, as if each specific combination were explicitly disclosed. The Figures and Examples are representative only and should not be interpreted as exclusive, or limiting the scope of the various embodiments disclosed herein.

BRIEF DESCRIPTION OF THE DRAWINGS

FIG. 5 represents the comparative in vivo pharmacokinetic profiles of controlled release pharmaceutical dosage form of doxycycline described in Example 6 and the reference product as measured in a single dose study.

FIG. 6B represents the comparative in vivo pharmacokinetic profiles of controlled release pharmaceutical dosage form of doxycycline described in Example 7B and the reference product as measured in a single dose study.

DETAILED DESCRIPTION

Figure 1:
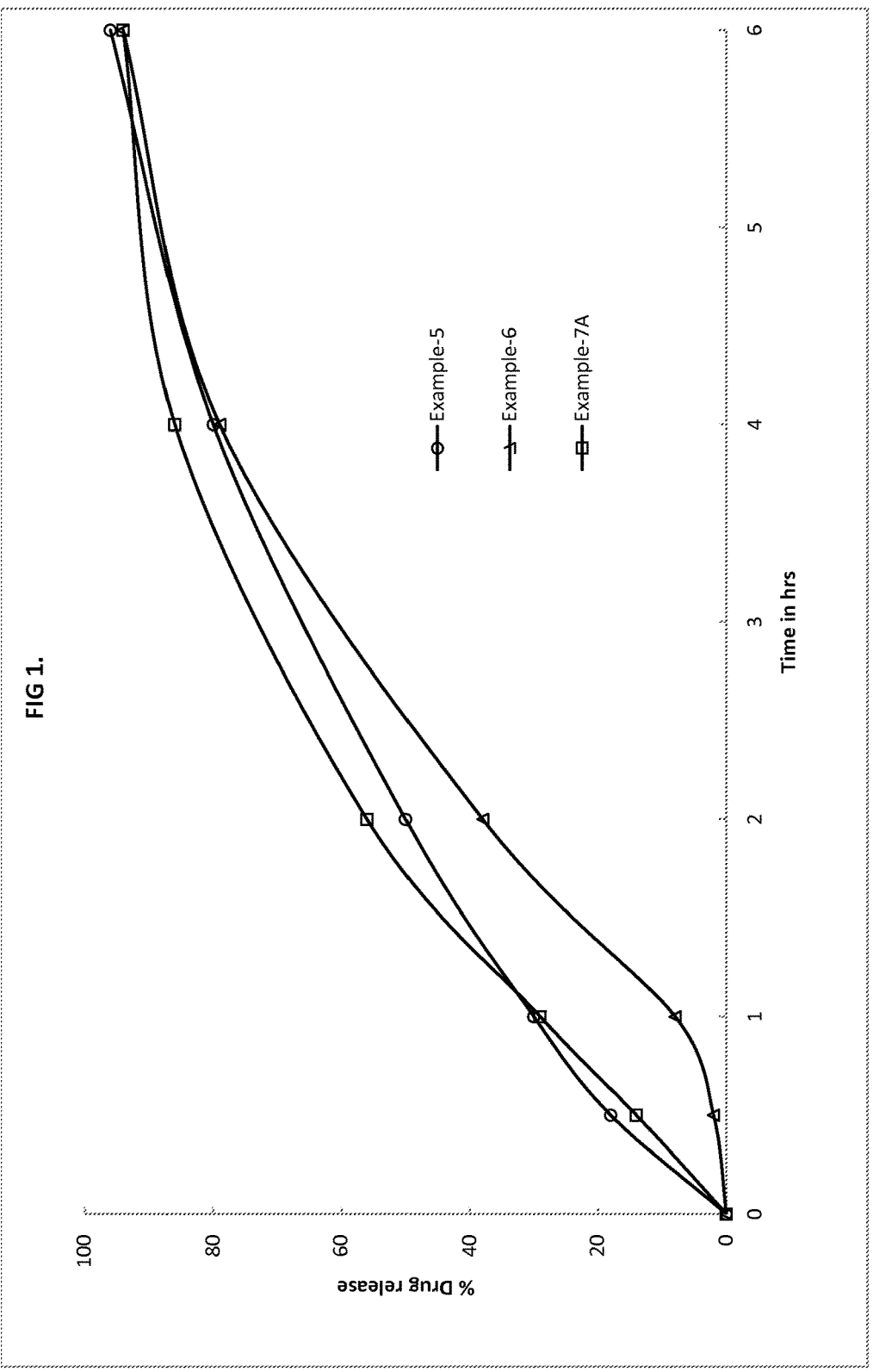
FIG. 1 represents the dissolution profile of controlled release pharmaceutical dosage forms of doxycycline described in Examples 5, 6, and 7A in 0.1N HCl, Basket apparatus at 100 rpm.
Figure 2:
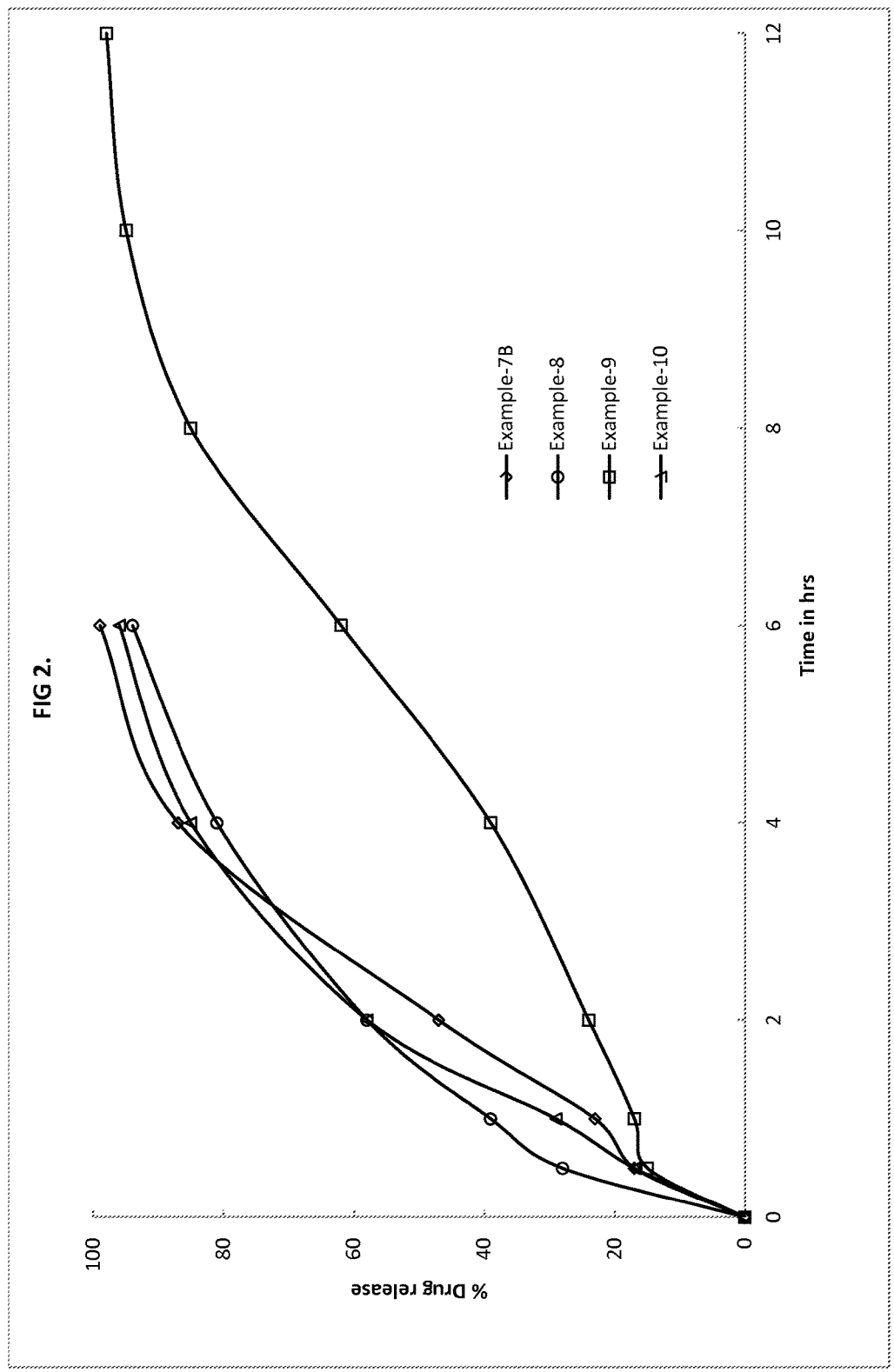
FIG. 2 represents the dissolution profile of controlled release pharmaceutical dosage forms of doxycycline described in Examples 7B, 8, 9, and 10 in 0.1N HCl, Basket apparatus at 100 rpm.

The indefinite articles "a" and "an" and the definite article "the" are intended to include both the singular and the plural, unless the context in which they are used clearly indicates otherwise.

The term "therapeutically effective amount" means the amount of the drug which halts or reduces the progress of the condition being treated or which otherwise completely or partly cures or acts palliatively on the condition. The therapeutically effective amount will vary depending on the subject being treated, the severity of the disease state, and the manner of administration.

As used herein the term "doxycycline" includes doxycycline free base, doxycycline monohydrate, and in some embodiments, pharmaceutically acceptable acid addition salts of doxycycline (e.g. doxycycline hydrochloride hemiethanolate hemihydrate), as well as all crystalline and amorphous forms of each of the foregoing.

Despite the known efficacy of certain tetracycline dosage forms for the treatment of dermatological disorders, stomach voiding and intestinal peristaltic movements limit the time that these drugs and/or oral dosage forms comprising these drugs remain in the upper portion of the gastrointestinal tract. For some drugs, such limited residence time in the upper portion of the gastrointestinal tract is unimportant because the drug's site of absorption may be lower in the gastrointestinal tract. However, for drugs such as doxycycline that are believed to have a site of absorption in the upper gastrointestinal tract and/or be better absorbed in this portion of the gut, such rapid displacement often requires larger doses of the drug to arrive at the desired bioavailability or systemic PK profile.

Aspects of the disclosure provided herein address the need for formulations capable of retaining particular drugs in the upper portion of the gastrointestinal tract.

In certain embodiments, the present disclosure provides a controlled release pharmaceutical dosage form comprising a therapeutically effective amount of doxycycline and one or more excipients and/or other formulating agents, wherein the dosage form is formulated to increase the residence time of the dosage form and/or doxycycline in a desired portion of gastrointestinal tract.

In certain embodiments, the pharmaceutical dosage form is formulated to remain in the upper portion of the gastrointestinal tract, such as the stomach and/or the duodenum, in order to increase systemic bioavailability of drug included in the dosage form. In particular embodiments, the pharmaceutical dosage form is formulated such that doxycycline is maintained in the upper portion of the gastrointestinal tract so that the bioavailability of the drug is increased. Retention of the pharmaceutical dosage form in the desired portion of the GI tract can be achieved by delaying the expulsion of the dosage form from the gastrointestinal tract using techniques such as bioadhesion, floatation, swelling, or a combination of any of the foregoing.

"Bioadhesion" is defined as the ability of a material to adhere to a biological tissue or structure, such as a mucous membrane. Bioadhesion is one solution to the problem of inadequate residence time resulting from stomach emptying and intestinal peristalsis, and from displacement by ciliary movement. Bioadhesive properties of polymers are affected by both the nature of the polymer and by the nature of the surrounding media. As used herein, the term "bioadhesive" refers to those compounds that affect bioadhesion. The term bioadhesive can be used interchangeably with the term "mucoadhesive." Exemplary bioadhesives include, but are not limited to, natural or synthetic materials, including macromolecules, polymers, oligomers, and mixtures thereof, that can adhere to a mucous membrane. Numerous bioadhesive molecules and polymers are known to those of ordinary skill in the art. Bioadhesion can be measured using a tensiometric method described elsewhere herein, and in particular embodiments, the peak detachment force of a dosage form described herein can be at least about 500 mN within 10 minutes of hydration, at least about 750 mN within 10 minutes of hydration, at least about 1000 mN within 10 minutes of hydration, or at least about 1300 mN within 10 minutes of hydration. In other embodiments, the peak detachment force can be at least about 1000 mN after 60 minutes of hydration, at least about 1100 mN after 60 minutes of hydration, at least about 1250 mN after 60 minutes of hydration, or at least about 1500 mN after 60 minutes of hydration.

In another embodiments, the present disclosure also provides floating drug delivery systems. Floating drug delivery systems can be prepared by using effervescent or non-effervescent excipients. Non-effervescent excipients can be gel-forming agents that entrap air and confer buoyancy to a dosage form upon gelling. Effervescent excipients are gas releasing agents that gasify upon contact with gastric fluids, releasing carbon dioxide which can be entrapped in a gelled hydrocolloid, or other material suitable for gas entrapment, thereby generating bouyancy.

Swellable drug delivery systems are dosage forms that swell upon contact with gastric fluid. The swelling enlarges the dosage form, slowing passage through the pyloric sphincter thereby maintaining the dosage form in the stomach for some additional period of time. In certain embodiments, the drug is released in the stomach either by erosion of the dosage form or by the diffusion of the drug from the dosage form or a combination of erosion and diffusion mechanisms. In particular embodiments, the dosage form herein can swell by at least about 1% to at least about 500% of its original volume, and in certain embodiments can swell by at least about 1%, at least about 10%, at least about 20%, at least about 30%, at least about 40%, at least about 50%, at least about 60%, at least about 70%, at least about 80%, at least about 90%, at least about 100%, at least about 125%, at least about 150%, at least about 175%, and in other embodiments, at least about 200% or even 500% of its original volume. Swelling can be measured using procedures described elsewhere herein.

In another aspect, the present disclosure provides therapeutic methods that include administering a therapeutic amount of a dosage form described herein. The dosage forms disclosed herein can be administered according to any suitable dosing strategy. In one embodiment, the dosage form can be administered orally once daily or twice daily. In other embodiments, the dosage forms described herein can be administered once every other day or once every three days. In particular embodiments, the dosage forms described herein are administered once daily.

Dosage

In particular embodiments, the purpose of the dosage forms disclosed herein is to orally deliver doxycycline such that the systemic levels of doxycycline are maintained at or above the desired therapeutic levels throughout the duration of treatment without any drastic fluctuations during a chronic treatment regimen. This stands in stark contrast to the systemic levels obtained following treatment with an oral immediate release dosage form, which typically shows peak levels of doxycycline within 2-3 hours of administration due to the burst release of the drug from the dosage form. In certain embodiments, the dosage form described herein can provide doxycycline oral bioavailability at a level greater than or equal to 80% relative to about an equal dose of an oral immediate release dosage form. In other embodiments, the dosage form described herein can provide doxycycline oral bioavailability at a level greater than or equal to 90%, 95%, 99%, and in some instances 99.9% relative to about an equal dose of an oral immediate release dosage form. In each of the above embodiments, the relative bioavailability is provided without the burst release observed in an immediate release oral doxycycline formulation.

The amount of doxycycline included in the dosage forms described herein can vary from about 10 to about 200 mg, including all amounts there between. In particular embodiments, the dosage form includes about 50 to about 200 mg doxycycline. In other embodiments, the dosage form can include about 60 to about 180 mg doxycycline. In still other embodiments, the dosage form can include about 100 to about 150 mg of doxycycline. In particular embodiments, the dosage form can include about 30, about 35, about 40, about 45, about 50, about 55, about 60, about 65, about 70, about 75, about 80, about 85, about 90, about 95, or about 100 mg of doxycycline. For purposes of clarity, all amounts or weights of doxycycline referenced in this application are referenced based on the equivalent amount of doxycycline freebase. Thus, a dosage form containing about 104 mg of doxycycline monohydrate would be understood to be a dosage form including about 100 mg doxycycline.

Bioavailability and Dissolution

In certain embodiments, the present disclosure provides a controlled release pharmaceutical dosage form wherein a) the dosage form is formulated to increase the residence time of the dosage form and/or doxycycline in the upper portion of the gastrointestinal tract; and b) the dosage form has an adhesive strength, measured as a force of detachment, of at least about 100 mN and in certain embodiments at least about 400 mN when measured using advanced force gauge equipment as described elsewhere herein.

In certain embodiments, the present disclosure provides a controlled release pharmaceutical dosage form of doxycycline wherein the dosage form is formulated to increase the residence time of the dosage form and/or doxycycline in the upper portion of the gastrointestinal tract and to release doxycycline from the dosage form over a period of at least about 4 to about 24 hours, and in certain embodiments, over a period of at least about 4 hours to about 20 hours, about 4 hours to about 16 hours, about 4 hours to about 12 hours, about 4 hours to about 8 hours, and about 4 hours to about 6 hours.

In certain embodiments, the present disclosure provides a controlled release pharmaceutical dosage form comprising doxycycline, wherein the controlled release pharmaceutical dosage form has a doxycycline release profile wherein about 10-20% of the doxycycline is released in about 30 mins, about 10-40% of the doxycycline is released in about 1 hour, about 20 to about 70% of the doxycycline is released in about 2 hours, about 50 to about 90% of the doxycycline is released in about 4 hours, and at least about 90% of the doxycycline is released in about 6 hours when measured using a USP Basket apparatus in 900 ml of 0.1 N HCl at 100 rpm.

In certain embodiments, the present disclosure provides a controlled release pharmaceutical dosage form comprising doxycycline wherein the controlled release pharmaceutical dosage form has a doxycycline release profile wherein about 15% of the doxycycline is released in about 30 mins, about 10 to about 25% of the doxycycline is released in about 1 hour, about 20 to about 60% of the doxycycline is released in about 2 hours, about 50 to about 90% of the doxycycline is released in about 4 hours, and more than about 90% of the doxycycline is released in about 6 hours when measured using a USP Basket apparatus in 900 ml of 0.1 N HCl at 100 rpm.

In certain embodiments, the present disclosure provides a controlled release pharmaceutical dosage form comprising doxycycline wherein the controlled release pharmaceutical dosage form has a doxycycline release profile wherein about 5 to about 20% of the doxycycline is released in about 30 mins, about 10 to about 25% of the doxycycline is released in about 1 hour, about 15 to about 35% of the doxycycline is released in about 2 hours, about 25 to about 50% of the doxycycline is released in about 4 hours, about 40 to about 70% of the doxycycline is released in about 6 hours, about 70 to about 90% of the doxycycline is released in about 8 hours and more than about 90% of the doxycycline is released in about 10 to about 12 hours when measured using a USP Basket apparatus in 900 ml of 0.1 N HCl at 100 rpm.

In certain embodiments, the present disclosure provides a controlled release pharmaceutical dosage form comprising doxycycline wherein the controlled release pharmaceutical dosage form has a doxycycline release profile wherein about 10 to about 50% of the doxycycline is released in about 1 hour, about 30 to about 70% of the doxycycline is released in about 2 hours, at least about 60% of the doxycycline is released in about 4 hours and at least about 80% of the doxycycline is released in about 6 hours when measured using a USP Paddle apparatus in 900 ml of 0.1 N HCl at 75 rpm.

In certain embodiments, the present disclosure provides a controlled release pharmaceutical dosage form comprising doxycycline wherein the controlled release pharmaceutical dosage form has a doxycycline release profile wherein about 5 to about 25% of the doxycycline is released in about 1 hour, about 50 to about 70% of the doxycycline is released in about 4 hours and about 90 to about 100% of the doxycycline is released in about 8 to about 12 hours when measured using a USP Paddle apparatus in 900 ml of 0.1N HCl at 75 rpm.

In certain embodiments, the present disclosure provides a controlled release pharmaceutical dosage form comprising doxycycline wherein the controlled release pharmaceutical dosage form has a doxycycline release profile wherein about 10% of the doxycycline is released in about 1 hour, about 40 to about 70% of the doxycycline is released in about 8 hours and about 90 to about 100% of the doxycycline is released in about 24 hours when measured using a USP Paddle apparatus in 900 ml of 0.1 N HCl at 75 rpm.

In certain embodiments, the present disclosure provides a method for reducing the side effects associated with the ingestion of doxycycline comprising administering to a patient in need thereof a pharmaceutical dosage form comprising doxycycline wherein the dosage form is formulated to increase the residence time of the dosage form and/or doxycycline in the gastrointestinal tract such that i) the dosage form provides therapeutic blood concentrations of doxycycline over at least about 18 to about 24 hours; ii) the dosage form provides a peak blood plasma level ($C_{max}$) of doxycycline in about 3 to about 10 hours ($t_{max}$), and in certain embodiments in about 3 to about 8 hours ($t_{max}$), or in about 4 to about 6 hours ($t_{max}$); and (iii) the dosage form demonstrates relative oral bioavailability when compared to an immediate release doxycycline formulation of more than about 80%, and in certain embodiments, more than about 90%, more than about 95%, more than about 99%, or more than about 99.9%.

Methods of Treatment

Although doxycycline can be used to treat many known bacterial infections, doxycycline is also known to be efficacious in treating dermal conditions such as acne and rosacea. While the etiology of acne is not completely understood, it is widely recognized that the bacteria *P. acnes* is at least partially responsible for the formation of comedones and microcomedones associated with the condition. Although doxycycline dosage forms such as MONODOX® and DORYX®, have been prescribed as adjunctive therapy for acne, there is presently no approved doxycycline dosage form for the primary indication of acne. Similarly, the doxycycline dosage form ORACEA® has been shown to be efficacious for the treatment of papular/pustular rosacea. As with acne, the etiology of rosacea is not well understood, however, and without wishing to be bound by any particular theory, it is surmised that the efficacy of doxycycline for the treatment of rosacea is derived from its anti-inflammatory properties.

Despite the common prescription of doxycycline and other tetracycline antibiotics for the treatment of acne and rosacea, many physicians and regulatory bodies would prefer to reduce the quantity of antibiotic delivered to a given patient to decrease the incidence of antibiotic resistance and/or the side effects associated with these drugs. Such a reduction, however, is also associated with reduced efficacy, rendering the drug less suitable for treating the underlying disease condition.

The controlled release pharmaceutical dosage forms described herein, however, provide a novel solution to the problem of potential drug resistance and side effects. As described elsewhere herein, the presently described controlled release pharmaceutical dosage forms have controlled release and/or increased residence time in the upper portion of the gastrointestinal tract, increasing the bioavailability of doxycycline, while simultaneously allowing the quantity of doxycycline dosed to be reduced relative to the amount of immediate release doxycycline typically required to achieve a similar result in a patient suffering from acne or rosacea. Thus, in certain embodiments, the present specification provides methods of treating acne comprising administering any of the controlled release dosage forms described herein to a patient in need thereof. In other embodiments, the present specification provides methods of treating rosacea comprising administering any of the controlled release dosage forms described herein to a patient in need thereof.

In certain embodiments, the present disclosure provides a method for treatment of acne and/or rosacea comprising administering to a patient in need thereof a pharmaceutical dosage form comprising doxycycline wherein the dosage form is formulated to increase the residence time of the dosage form and/or control release of doxycycline in the upper portion of the gastrointestinal tract such that i) the dosage form provides therapeutic blood concentrations of doxycycline over at least about 18 to about 24 hours; ii) the dosage form provides a peak blood plasma level ($C_{max}$) of doxycycline in about 3 to about 10 hours ($t_{max}$) and in certain embodiments about 3 to about 8 hours ($t_{max}$) or in about 4 to about 6 hours ($t_{max}$) and (iii) the dosage form demonstrates relative oral bioavailability when compared to an immediate release doxycycline formulation of more than about 80% and in certain embodiments, more than about 90%.

Excipients and Other Formulating Agents

As discussed elsewhere herein, the controlled release pharmaceutical dosage form comprising a therapeutically effective amount of doxycycline also includes one or more excipients and/or other formulating agents. Suitable excipients and other formulating agents include, but are not limited to, release rate controlling agents, bioadhesive and/or mucoadhesive agents, swelling agents, binders, diluents, disintegrants, pore forming agents, lubricants, stabilizing agents, surfactants, plasticizers, anti-tacking agents, glidants, solubilizing agents, gas generating agents, solvents, as well as combinations thereof. In certain embodiments, a given excipient and/or formulating agents can perform more than one function.

Release rate controlling agents suitable for use in the present controlled release pharmaceutical dosage forms include, but are not limited to, hydrophilic release controlling agents, hydrophobic release controlling agents, and mixtures thereof.

Exemplary hydrophilic release controlling agents include, but are not limited to optionally-substituted cellulosic polymers having the general structure:

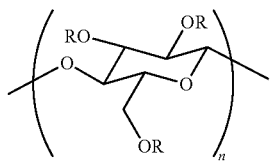

wherein each R can be independently selected from the group consisting of H, $CH_3$, $CH_2CH_2OH$, $CH_2CO_2H$, and $CH_2CH(OH)CH_3$. Exemplary optionally-substituted cellulosic polymers include, but are not limited to, hydroxypropyl methyl cellulose (HPMC or hypromellose), hydroxypropyl cellulose (HPC), carboxymethyl cellulose, and hydroxyethyl cellulose (HEC). Additional exemplary release controlling agents include, but are not limited to, ethylene glycol oligomers such as polyethylene oxide and polyethylene glycol; vinyl polymers such as polyvinyl alcohol and polyvinylpyrrolidone (PVP or povidone); gums such as xanthan gum and guar gum; naturally occurring polysaccharides such as carrageenan, sodium alginate and chitosan and its derivatives; polyacrylic acid polymers such as carbomer.

Exemplary hydrophobic release controlling agents include, but are not limited to, polyvinyl acetate; ethyl cellulose; and cellulose esters (e.g. cellulose acetate; cellulose propionate (lower, medium, or higher molecular weight), cellulose acetate propionate; cellulose acetate butyrate; cellulose acetate phthalate; and cellulose triacetate).

Other exemplary hydrophobic release controlling agents include, but are not limited to copolymers of methyl (or ethyl) acrylate, methyl methacrylate, and a methacrylic acid ester having a quaternary amine present (e.g. EUDRAGIT® RL 100, EUDRAGIT® RL PO (Poly(ethyl acrylate-co-methyl methacrylate-co-trimethylammonioethyl methacrylate chloride) 1:2:0.2), EUDRAGIT® RL 30 D, EUDRAGIT® RL 12.5, EUDRAGIT® RS 100, EUDRAGIT® RS PO, EUDRAGIT® RS 30 D, EUDRAGIT® RS 12.5, EUDRAGIT® NE 30 D, EUDRAGIT® NE 40 D, and EUDRAGIT® NM 30 D, all manufactured by Evonik Industries, Rellinghauser Straβe 1-11, 45128 Essen, Germany).

Further exemplary hydrophobic release controlling agents include, but are not limited to, poly methacrylates (e.g. poly (methyl methacrylate), poly (ethyl methacrylate), poly (butyl methacrylate), poly (isobutyl methacrylate), and poly (hexyl methacrylate), poly (isodecyl methacrylate), poly (lauryl methacrylate), poly (phenyl methacrylate), poly (methyl acrylate), poly (isopropyl acrylate), poly (isobutyl acrylate), poly (octadecyl acrylate)).

Waxes are also suitable for use as hydrophobic release controlling agents. Exemplary waxes include, but are not limited to, beeswax, carnauba wax, paraffin wax, microcrystalline wax, and ozokerite.

Fatty alcohols may also be used as hydrophobic release controlling agents. Exemplary fatty alcohols include, but are not limited to, cetostearyl alcohol, stearyl alcohol, cetyl alcohol and myristyl alcohol.

Hydrophobic release controlling agents can also be fatty acid esters such as, but not limited to, glyceryl monostearate, glycerol monooleate, acetylated monoglycerides, tristearin, tripalmitin, cetyl esters wax, glyceryl palmitostearate, glyceryl behenate, hydrogenated vegetable oils.

A given formulation can include one or more than one hydrophobic release controlling agent and can thus include a mixture of any of the foregoing hydrophobic release controlling agents.

The amount of the release rate controlling agent can be any suitable amount and in certain embodiments can range from about 5% to about 70% w/w, and in certain embodiments, from about 5% to about 50% w/w, or from about 5% to about 35% w/w based on the total weight of the controlled release pharmaceutical dosage form.

Mucoadhesive and/or bioadhesive agents suitable for use in the present invention include, but are not limited to, natural polymers such as pectin, zein, modified zein, casein, gelatin, gluten, serum albumin, collagen, chitosan, oligosaccharides and polysaccharides such as cellulose, dextrans, tamarind seed polysaccharide, gellan, carrageenan, xanthan gum, gum Arabic, hyaluronic acid, polyhyaluronic acid, alginic acid, and sodium alginate; synthetic polymers such as polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polylactides, poly(butyric acid), poly(valeric acid), poly(lactide-co-glycolide), polyanhydrides, polyorthoesters, poly(fumaric acid), poly(maleic acid); and blends and copolymers or mixtures of any of the foregoing. The release rate controlling agents can also be used as mucoadhesive and/or bioadhesive agents, depending upon the inherent properties of the release rate controlling agent. As noted elsewhere herein, the level of mucoadhesion can be measured and can be within the ranges specified herein.

In addition to the release rate controlling agents that can also serve as mucoadhesive and/or bioadhesive agents, further exemplary mucoadhesive and/or bioadhesive agents can also include polymers having a hydrophobic backbone with at least one hydrophobic group pendant from the backbone. Suitable hydrophobic groups include, but are not limited to, groups that are generally non-polar, such as alkyl, alkenyl, and alkynyl groups. Preferably, the hydrophobic groups are selected to enhance bioadhesion and/or mucoadhesion.

A further group of polymers suitable for use as bioadhesive and/or mucoadhesive agents includes polymers having a hydrophobic backbone with at least one hydrophilic group pendant from the backbone. Suitable hydrophilic groups include groups that are capable of hydrogen bonding or electrostatically bonding to another functional group. Examples of such hydrophilic groups include negatively charged groups such as carboxylates, sulfonates, and phosphonates; positively charged groups such as protonated amines; and neutral, polar groups, such as amides and imines. In certain embodiments, the hydrophilic groups are selected to enhance bioadhesion and/or mucoadhesion.

Swelling agents suitable for use in the present dosage forms include, but are not limited to, crosslinked poly (acrylic acid) (e.g., Carbomers 934, 940, 941, and 974P), poly(alkylene oxide) (e.g., polyethyleneoxide), polyvinyl alcohol, polyvinyl pyrrolidone, hydrogel, maleic anhydride polymers, cellulose polymers, polysaccharides, starches, starch based polymers, and mixtures thereof. Swelling agents can themselves swell or, alternatively, can be swelling aids. Swelling aids are agents that do not swell (or only swell minimally) but aid another swelling agent in swelling.

The amount of the mucoadhesive and/or bioadhesive polymer in the pharmaceutical dosage form described herein can be any acceptable amount and in certain embodiments may range from about 0.1% to about 75% w/w, from about 5% to about 50% w/w, and in still other embodiments, from about 5% to about 35% w/w based on the total weight of the controlled release pharmaceutical dosage form.

In certain embodiments, the controlled release pharmaceutical dosage form can also comprise one or more coatings. The one or more coatings may be applied with a tablet coater using coating solutions prepared from aqueous or non-aqueous solvent systems or the combinations thereof. The controlled release pharmaceutical dosage forms can also be coated by compression coating and coating in a fluidized bed. Such methods are well known to those skilled in the art.

Agents suitable for use as coating materials for the controlled release pharmaceutical dosage form described here include, but are not limited to, alkyl celluloses such as methyl or ethyl cellulose, hydroxyalkylcelluloses, polyvinylpyrrolidone, polysaccharides, acacia, sucrose, gelatin, shellac, cellulose acetate pthalate, lipids, acrylic polymers, polyvinyl alcohol, copolymers of vinylpyrrolidone and vinyl acetate, and mixtures of any of the foregoing.

In particular embodiments, the coating material can be a controlled release film coating material that can form a semipermeable membrane or coating, which can be porous or non-porous, and which is permeable to external fluid, and substantially impermeable to unsolubilized drug contained within a core. Typically, external fluids are aqueous fluids or biological fluids in the environment of use, such as gastric fluid present in the upper gastrointestinal tract. Materials useful as controlled release film coating material that can form a semipermeable membrane or coating can be substantially insoluble in an external fluid. In other embodiments, the materials useful for forming the semipermeable membrane or coating can erode after a predetermined period of time. Exemplary materials useful in forming the semipermeable membrane or coating include, but are not limited to, acetaldehyde dimethyl acetate; acetaldehyde dimethylcellulose acetate; agar acetate; alkylene oxide and alkyl glycidyl ether copolymers; amylose triacetate; beta glucan acetate; beta glucan triacetate; cellulosic materials such as cellulose esters, cellulose ethers, cellulose ester-ether polymers, mono-, di- and tricellulose acrylates, mono-, di- and tricellulose alkenylates; hydroxylated ethylene-vinyl acetate; selectively permeable aromatic nitrogen containing polymeric membranes; polyamides; polyalkylene oxides; polyether and polyamide copolymers; polyglycolic acid and polylactic acid and derivatives thereof; polymeric epoxides; poly(methacrylate) copolymer salts; cross-linked poly(sodium styrene sulfonate); crosslinked polystyrenes; polyurethanes; polyvinyl alcohol; crosslinked poly(vinylbenzyltrimethyl ammonium chloride); poly(vinylmethyl ether) copolymers; polyvinylpyrrolidone; propylcarbamate; sulfonated polystyrenes; triacetate of locust gum bean; and combinations of any of the foregoing.

In other embodiments, the coating material can be a rupturable coating system that uses osmotic force to rupture an enteric membrane to reveal an underlying dosage form. In other embodiments, non-permeable coatings of insoluble polymers, such as cellulose acetate and ethylcellulose, can be used as enteric coatings providing delayed/modified release by inclusion of soluble pore forming agents in the coating. Exemplary pore forming agents include, but are not limited to, sodium chloride, potassium chloride, low viscosity hypromellose, polyethylene glycol, sodium lauryl sulphate, and combinations of the foregoing.

The coating materials can constitute any acceptable amount of the dosage form, and in particular embodiments from about 1% to about 20% w/w, from about 1.5% to about 15% w/w, or from about 2% to about 10% w/w, based on total weight of the controlled release pharmaceutical dosage form.

In certain embodiments, the coating material can be mixed with one or more plasticizers or thermoplastic polymers. Plasticizers and thermoplastic polymers typically increase the strength and/or reduce the brittleness of the polymeric coatings. Exemplary plasticizers include, but are not limited to, dibutyl sebacate, polyethylene glycol, triethyl citrate, dibutyl adipate, dibutyl fumarate, diethyl phthalate, ethylene oxide-propylene oxide block copolymers, di(sec-butyl) fumarate, and mixtures thereof. In embodiments where a plasticizer is used, the amount of the plasticizer can be any acceptable amount, and in particular embodiments may range from about 0.05% to about 5% w/w, from about 0.1% to about 2% w/w, and in other embodiments, from about 0.2% to about 1% w/w based on the total weight of the controlled release pharmaceutical dosage form.

Pharmaceutically acceptable binders suitable for use in the controlled release pharmaceutical dosage form may include, but are not limited to, starches, gums, polyvinylpyrrolidone, syrup, polyethylene oxide, polyacrylamide, poly-N-vinyl amide, sodium carboxymethylcellulose, methylcellulose, polyethylene glycol, gelatin, polyethylene oxide, polypropylene glycol, and mixtures thereof. The amount of binder may range from about 0.5% to about 20% w/w, from about 1% to about 15% w/w, and in other embodiments, from about 2.0% to about 10.0% w/w based on the weight of the controlled release pharmaceutical dosage form.

Pharmaceutically acceptable diluents suitable for use in the controlled release pharmaceutical dosage form described herein may include, but are not limited to, carbohydrates, polyols, sugar alcohols (e.g. mannitol), carbonate, sulphate or phosphate salts of inorganic metals, and mixtures of any of the foregoing. The amount of diluent may be any acceptable amount, and in certain embodiments ranges from about 5% to about 95% w/w, from about 10% to about 90% w/w, and in other embodiments, from about 15% to about 75% w/w based on the weight of the controlled release pharmaceutical dosage form.

Pharmaceutically acceptable disintegrants suitable for use in the controlled release pharmaceutical dosage form may include, but are not limited to, starches (e.g., sodium starch glycolate, partially pregelatinized starch, etc.), clays, celluloses, alginates, gums, cross-linked polymers (e.g., cross-linked polyvinyl pyrrolidone or crospovidone, cross-linked sodium carboxymethylcellulose or croscarmellose sodium, cross-linked calcium carboxymethylcellulose, soy polysaccharides), and mixtures of any of the foregoing. The amount of disintegrant may be any acceptable amount, and in certain embodiments can range from about 0% to about 30% w/w, from about 1% to about 20% w/w, and in other embodiments from about 2% to about 15% w/w based on the weight of the controlled release pharmaceutical dosage form.

Pharmaceutically acceptable lubricants suitable for use in the controlled release pharmaceutical dosage form may include, but are not limited to, metal salts of stearic acid (e.g., magnesium stearate, aluminium stearate, zinc stearate, and calcium stearate), polyethylene glycol, mineral oil, sodium stearyl fumarate, stearic acid, hydrogenated vegetable oil, glyceryl behenate, glyceryl palmitostearate, glyceryl stearate, cornstarch, talc, calcium silicate, magnesium silicate, colloidal silicon dioxide, silicon hydrogel, and mixtures thereof. The amount of lubricant can be any acceptable amount, and in certain embodiments may range from about 0.1% to about 10% w/w, from about 0.2% to about 7% w/w, and in other embodiments, from about 0.5% to about 5% w/w based on the weight of the controlled release pharmaceutical dosage form.

Pharmaceutically acceptable stabilizing agents suitable for use in the controlled release pharmaceutical dosage form may include, but are not limited to, antioxidants, adsorbents, absorbents, buffers, chelating agents, sequestering agents, and mixtures thereof. The amount of stabilizing agent can be any acceptable amount and in certain embodiments may range from about 0.1% to about 10% w/w, from about 0.2% to about 7% w/w, and in other embodiments from about 0.5% to about 5% w/w based on the weight of the controlled release pharmaceutical dosage form.

Pharmaceutically acceptable surfactants suitable for use in the controlled release pharmaceutical dosage form may include, but are not limited to, poloxamer, dioctyl sodium sulfosuccinate, triethanolamine, sodium lauryl sulphate, polyoxyethylene sorbitan and poloxalkol derivatives, quaternary ammonium salts, and mixtures thereof. The surfactant may be selected from ionic or non-ionic or zwitterionic surfactants. The amount of surfactant can be any acceptable amount and in certain embodiments may range from about 0.1% to about 10% w/w, from about 0.2% to about 7% w/w, and in other embodiments, from about 0.5% to about 5% w/w based on the weight of the controlled release pharmaceutical dosage form.

Pharmaceutically acceptable anti-tacking agents suitable for use in the controlled release pharmaceutical dosage form may include, but are not limited to, talc, stearic acid, magnesium stearate, colloidal silicon dioxide, and mixtures thereof. The amount of anti-tacking agent can be any acceptable amount and in certain embodiments may range from about 0.1% to about 10% w/w, from about 0.2% to about 7% w/w, and in other embodiments, from about 0.3% to about 5% w/w based on the weight of the controlled release pharmaceutical dosage form.

Pharmaceutically acceptable glidants suitable for use in the controlled release pharmaceutical dosage form may include, but are not limited to, silicon dioxide, colloidal silica, powdered cellulose, talc, tribasic calcium phosphate, and mixtures thereof. The amount of glidant can be any acceptable amount and in certain embodiments may range from about 0.1% to about 10% w/w, from about 0.2% to about 7% w/w, and in other embodiments, from about 0.5% to about 5% w/w based on the weight of the controlled release pharmaceutical dosage form.

Pharmaceutically acceptable solubilizing agents suitable for use in the controlled release pharmaceutical dosage form may include, but are not limited to, cyclodextrins, vitamin E and its derivatives such as vitamin E TPGS; monohydric alcohol esters such as trialkyl citrates; lactones and lower alcohol fatty acid esters; nitrogen-containing solvents; phospholipids; glycerol acetates such as acetin, diacetin, and triacetin; glycerol fatty acid esters such as mono, di-, and triglycerides and acetylated mono- and diglycerides; propylene glycol esters; ethylene glycol esters; and mixtures of any of the foregoing. The amount of solubilizing agents can be any acceptable amount and in certain embodiments may range from about 0.1% to about 10% w/w, from about 0.2% to about 7% w/w, and in other embodiments, from about 0.5% to about 5% w/w based on the weight of the controlled release pharmaceutical dosage form.

Pharmaceutically acceptable gas generating agents suitable for use in the controlled release pharmaceutical dosage form may include, but are not limited to, sodium bicarbonate, citric acid, tartaric acid, and mixtures thereof. The amount of gas generating agents can be any acceptable amount and in certain embodiments may range from about 0.5% to about 20% w/w, from about 1% to about 15% w/w, and in certain embodiments from about 1.5% to about 10% w/w based on the weight of the controlled release pharmaceutical dosage form.

Pharmaceutically acceptable solvents suitable for use in the preparation of the controlled release pharmaceutical dosage form may include, but are not limited to, aqueous solvents such as water and aqueous buffer solutions, non-aqueous solvents such as acetonitrile, chloroform, cyclohexane, 1,2-dichloroethene, 1,2-dimethoxyethane, N,N-dimethylacetamide, N,N-dimethylformamide, 1,4-dioxane, 2-ethoxyethanol, ethylene glycol, formamide, hexane, methanol, methylene chloride, N-methylpyrrolidone, tetrahydrofuran, trichloroethylene, xylene, acetone, anisole, 1-butanol, 2-butanol, ethanol, ethyl acetate, ethyl ether, heptane, isobutyl acetate, isopropyl acetate, 1,1-dimethoxymethane, isopropyl ether, methyltetrahydrofuran, and mixtures thereof.

Pharmaceutically acceptable solubilizing agents suitable for use in the controlled release pharmaceutical dosage form may include, but are not limited to, salicylates, sodium salicylates, medium and long chain glycerides, bile salts such as sodium taurocholate, sodium taurodeoxycholate, taurodihydrofusidate, surfactants such as sodium dodecyl sulphate, sodium dodecyl sulfosuccinate, chelating agents such as EDTA, EGTA, chitosan salts, N-trimethyl chitosan chloride, poly (acrylic acid) derivatives, vitamin E TPGS, polyvinyl pyrolidone, and combinations of the foregoing.

Exemplary Controlled Release Pharmaceutical Dosage Forms

The controlled release pharmaceutical dosage forms described herein are formulated to provide a gradual release of the drug over a given period of time and/or control the location of release so that the concentration of the released drug is maintained in the blood for a longer time at a more uniform concentration than a corresponding immediate release dosage forms comprising the same drug in the same amount.

The controlled release pharmaceutical dosage form described herein can use one or more forms of controlled release systems or mechanisms, e.g., matrix type controlled release, reservoir type controlled release, membrane diffusion controlled release, site targeted release, osmotically controlled release, pH dependent delayed release, timed release, and combinations thereof. The controlled release pharmaceutical dosage form can also include one or more immediate release components. The controlled release aspects of the controlled release pharmaceutical dosage form can also act to extend release, sustain release, delay release, and/or cause a pulsed-type release.

In some embodiments, the controlled release pharmaceutical dosage form can be in the form of a tablet. Tablets can include, but are not limited to, single layer tablets, multilayer tablets, mini tablets, bioadhesive tablets, caplets, matrix tablets, tablets within a tablet, tablets within capsules, and mucoadhesive tablets. In one embodiment, the controlled release pharmaceutical dosage form comprises a tablet having at least one controlled release layer and one bioadhesive layer, wherein the controlled release layer and the bioadhesive layer comprise one or more excipients and/or other formulating agents suitable to affect delivery of an active ingredient (e.g. doxycycline) at a desired location within the gastrointestinal tract. In certain embodiments, the active ingredient is present in at least one of the controlled release layer or the bioadhesive layer. In particular embodiments, the active ingredient is present in the controlled release layer. In other embodiments, the controlled release pharmaceutical dosage form can include one or more immediate release layers in addition to the controlled release layer and the bioadhesive layer. In certain embodiments, the relative proportion of the active ingredient in the immediate release layer to that of the controlled release layer can be in the range of from about 5 to about 95%, from about 5 to about 80%, from about 5 to about 70%, from about 5 to about 60%, from about 10 to about 50%, and in certain embodiments from about 10 to about 30%.

In another embodiment, the controlled release pharmaceutical dosage form comprises a tablet having at least a) a controlled release doxycycline layer comprising a first therapeutically effective amount of doxycycline and one or more pharmaceutically acceptable excipients; b) an immediate release doxycycline layer, wherein said immediate release doxycycline layer comprises a second therapeutically effective amount of doxycycline and one or more pharmaceutically acceptable excipients; and c) a bioadhesive and/or mucoadhesive layer which comprises at least one bioadhesive and/or mucoadhesive agent and optionally one or more pharmaceutically acceptable excipients. In certain embodiments, the controlled release doxycycline layer can optionally include immediate release or controlled release granules of doxycycline.

In another embodiment, the controlled release pharmaceutical dosage form comprises a tablet having a) a controlled release layer comprising a therapeutically effective amount of doxycycline and one or more pharmaceutically acceptable excipients wherein said controlled release layer provides a controlled release of doxycycline; b) an immediate release doxycycline layer comprising a therapeutically effective amount of doxycycline and one or more pharmaceutically acceptable excipients effective to provide an immediate release of the doxycycline in the immediate release layer; and c) a bioadhesive layer, wherein said bioadhesive layer comprises one or more bioadhesive and/or mucoadhesive agents and optionally one or more pharmaceutically acceptable excipients. In certain embodiments, the doxycycline in the controlled release layer can be in the form of particles coated with an enteric polymer. In other embodiments, the doxycycline in the controlled release layer can be a mixture of enterically coated and uncoated particles In another embodiment, the controlled release pharmaceutical dosage form comprises a tablet having a) a controlled release doxycycline layer comprising a first therapeutically effective amount of doxycycline and one or more pharmaceutically acceptable excipients wherein the controlled release doxycycline layer provides immediate release and controlled release of the first therapeutically effective amount of doxycycline; b) a second layer comprising a second therapeutically effective amount of doxycycline and one or more polymers wherein the second layer provides increased residence time of the controlled release pharmaceutical dosage form in the upper portion of the gastrointestinal tract; and c) optionally, a coating layer on the controlled release pharmaceutical dosage form. In certain embodiments, the optional coating layer can be an immediate release doxycycline overcoat. In other embodiments, the optional coating layer can be a bioadhesive and/or mucoadhesive coating.

In another embodiment, the controlled release pharmaceutical dosage form comprises a tablet having a) a first layer comprising a first therapeutically effective amount of doxycycline and one or more pharmaceutically acceptable excipients wherein the first layer provides an immediate release and controlled release of the first therapeutically effective amount of doxycycline; b) a second layer comprising a second therapeutically effective amount of doxycycline and one or more polymers wherein the second layer provides increased residence time of the controlled release pharmaceutical dosage form in the upper portion of the gastrointestinal tract; c) an enteric coating; and d) an immediate release doxycycline overcoat.

In another embodiment, the controlled release pharmaceutical dosage form comprises a core and a core coating, wherein the core coating provides for increased residence time of the controlled release pharmaceutical dosage form in the upper portion of the gastrointestinal tract. In this embodiment, the core can comprise doxycycline in a swellable polymer matrix. In some embodiments, the core coating can itself be coated with an immediate release doxycycline overcoat.

In another embodiment, the controlled release pharmaceutical dosage form comprises a tablet having a) a controlled release doxycycline layer which comprises a first therapeutically effective amount of doxycycline and one or more pharmaceutically acceptable excipients; b) a swellable gas generating layer which comprises a second therapeutically acceptable amount of doxycycline, one or more swellable polymers, and one or more gas generating agents wherein said layer provides increased residence of the controlled release pharmaceutical dosage form in the upper portion of the gastrointestinal tract; c) a permeable and/or expandable porous coating; and d) an immediate release doxycycline overcoat.

Floating Gastroretentive Formulations

In one embodiment, the controlled release pharmaceutical dosage form described herein can be a floating gastroretentive formulation and can include a controlled release doxycycline layer, a swellable and/or floating layer, an expandable porous coating, an optional seal coating, and an immediate release doxycycline overcoat. The controlled release doxycycline layer can include from about 5 to about 15 weight % doxycycline based on the total weight of the dosage form, from about 6 to about 13 weight % doxycycline based on the total weight of the dosage form, from about 7 to about 12% doxycycline based on the total weight of the dosage form, and from about 8 to about 10 weight % doxycycline based on the total weight of the dosage form. In particular embodiments, the controlled release doxycycline layer can include from about 8.5 to about 9.5 weight % doxycycline based on the total weight of the dosage form, and in certain embodiments about 9 to about 9.3 weight % doxycycline based on the total weight of the dosage form, and in still further embodiments, about 9.1 weight % doxycycline based on the total weight of the dosage form.

The controlled release doxycycline layer can further include one or more excipients and/or other formulating agents, such as one or more diluents, a binder, a pore forming agent, optionally one or more hydrophilic release controlling agents, and one or more pharmaceutically acceptable lubricants.

In certain embodiments, the controlled release doxycycline layer can include from about 15 weight % to about 25 weight % of a first diluent based on the total weight of the dosage form. In certain embodiments, the controlled release doxycycline layer can include from about 17 weight % to about 23 weight % of the diluent based on the total weight of the dosage form. In certain embodiments, the controlled release doxycycline layer can include about 17.7 weight % or about 22.6 weight % of the diluent based on the total weight of the dosage form. In certain embodiments, the diluent can be lactose monohydrate.

In certain embodiments, the controlled release doxycycline layer can include from about 5 weight % to about 25 weight % of a second diluent based on the total weight of the dosage form. In certain embodiments, the controlled release doxycycline layer can include from about 7 weight % to about 22 weight % of the second diluent based on the total weight of the dosage form. In certain embodiments, the controlled release doxycycline layer can include about 10 weight % to about 20 weight % of the second diluent based on the total weight of the dosage form. In certain embodiments, the controlled release doxycycline layer can include about 10.7 weight % or about 18.8 weight % of the second diluent based on the total weight of the dosage form. In certain embodiments, the second diluent can be mannitol.

In certain embodiments, the controlled release doxycycline layer can include from about 1 weight % to about 10 weight % of the pore forming agent based on the total weight of the dosage form. In certain embodiments, the controlled release doxycycline layer can include from about 2 weight % to about 7 weight % of the pore forming agent based on the total weight of the dosage form. In certain embodiments, the controlled release doxycycline layer can include about 3 weight % to about 5 weight % of the pore forming agent based on the total weight of the dosage form. In certain embodiments, the controlled release doxycycline layer can include about 4 weight % or about 4.3 weight % of the pore forming agent based on the total weight of the dosage form. In certain embodiments, the pore forming agent can be sodium chloride.

In certain embodiments, the controlled release doxycycline layer can optionally include from about 5 weight % to about 10 weight % of the hydrophilic release controlling agent based on the total weight of the dosage form. In certain embodiments, the controlled release doxycycline layer can optionally include from about 6 weight % to about 9 weight % of the hydrophilic release controlling agent based on the total weight of the dosage form. In certain embodiments, the controlled release doxycycline layer can optionally include from about 7 weight % to about 8 weight % of the hydrophilic release controlling agent based on the total weight of the dosage form. In certain embodiments, the controlled release doxycycline layer can optionally include about 7.5 weight % of the hydrophilic release controlling agent based on the total weight of the dosage form. In certain embodiments, the hydrophilic release controlling agent can be hypromellose.

In certain embodiments, the controlled release doxycycline layer can optionally include from about 1 weight % to about 5 weight % of the binder based on the total weight of the dosage form. In certain embodiments, the controlled release doxycycline layer can optionally include from about 2 weight % to about 4 weight % of the binder based on the total weight of the dosage form. In certain embodiments, the controlled release doxycycline layer can optionally include from about 3 weight % of the binder based on the total weight of the dosage form. In certain embodiments, the controlled release doxycycline layer can optionally include about 3.2 weight % of the binder based on the total weight of the dosage form. In certain embodiments, the binder can be Povidone K30.

In certain embodiments, the controlled release doxycycline layer can include from about 0.25 to about 1.5 weight % of the one or more pharmaceutically acceptable lubricants based on the total weight of the dosage form. In certain embodiments, the controlled release doxycycline layer can include from about 0.5 to about 1 weight % of the one or more pharmaceutically acceptable lubricants based on the total weight of the dosage form. In certain embodiments, the one or more pharmaceutically acceptable lubricants can be selected from magnesium stearate and colloidal silicon dioxide. In certain embodiments, the controlled release doxycycline layer can include from about 0.5 weight % colloidal silicon dioxide and about 0.5 weight % magnesium stearate, based on the total weight of the dosage form.

The swellable and/or floating layer can include one or more hydrophilic release controlling agents, one or more diluents, one or more binders, one or more pharmaceutically acceptable gas generating agents, and one or more pharmaceutically acceptable lubricants.

In certain embodiments, the swellable and/or floating layer can include from about 3 weight % to about 7 weight % of a first hydrophilic release controlling agent based on the total weight of the dosage form. In certain embodiments, the swellable and/or floating layer can include from about 4 weight % to about 6 weight % of the first hydrophilic release controlling agent based on the total weight of the dosage form. In certain embodiments, the swellable and/or floating layer can include from about 4.5 weight % to about 5.5 weight % of the first hydrophilic release controlling agent based on the total weight of the dosage form. In certain embodiments, the swellable and/or floating layer can include about 4.6 weight % or about 5.4 weight % of the first hydrophilic release controlling agent based on the total weight of the dosage form. In certain embodiments, the first hydrophilic release controlling agent is polyethylene oxide.

In certain embodiments, the swellable and/or floating layer can include from about 7 weight % to about 12 weight % of a second hydrophilic release controlling agent based on the total weight of the dosage form. In certain embodiments, the swellable and/or floating layer can include from about 8 weight % to about 11 weight % of the second hydrophilic release controlling agent based on the total weight of the dosage form. In certain embodiments, the swellable and/or floating layer can include from about 9 weight % to about 11 weight % of the second hydrophilic release controlling agent based on the total weight of the dosage form. In certain embodiments, the swellable and/or floating layer can include about 9.2 weight % or about 10.7 weight % of the second hydrophilic release controlling agent based on the total weight of the dosage form. In certain embodiments, the second hydrophilic release controlling agent can be hypromellose.

In certain embodiments, the swellable and/or floating layer can include from about 8 weight % to about 15 weight % of a diluent based on the total weight of the dosage form. In certain embodiments, the swellable and/or floating layer can include from about 9 weight % to about 13 weight % of the diluent based on the total weight of the dosage form. In certain embodiments, the swellable and/or floating layer can include from about 10 weight % to about 12 weight % of the diluent based on the total weight of the dosage form. In certain embodiments, the swellable and/or floating layer can include about 10.3 weight % or about 12.1 weight % of the diluent based on the total weight of the dosage form. In certain embodiments, the diluent can be lactose monohydrate.

In certain embodiments, the swellable and/or floating layer can include from about 5 weight % to about 7 weight % of the one or more pharmaceutically acceptable gas generating agents based on the total weight of the dosage form. In some embodiments, the swellable and/or floating layer can include from about 5.5 weight % to about 6.5 weight % of the one or more pharmaceutically acceptable gas generating agents based on the total weight of the dosage form. In certain embodiments, the swellable and/or floating layer can include from about 5.6 weight % to about 6.4 weight % of the one or more pharmaceutically acceptable gas generating agents based on the total weight of the dosage form. In certain embodiments, the swellable and/or floating layer can include from about 4 weight % to about 5 weight % of a first pharmaceutically acceptable gas generating agent based on the total weight of the dosage form. In certain embodiments, the swellable and/or floating layer can include from about 4.2 weight % to about 4.8 weight % of a first pharmaceutically acceptable gas generating agent based on the total weight of the dosage form. In certain embodiments, the first pharmaceutically acceptable gas generating agent can be about 4.2 weight % of the total dosage form. In other embodiments, the first pharmaceutically acceptable gas generating agent can be about 4.8 weight % of the total dosage form. In certain embodiments, the swellable and/or floating layer can include from about 1.2 weight % to about 1.8 weight % of a second pharmaceutically acceptable gas generating agent based on the total weight of the dosage form. In certain embodiments, the second pharmaceutically acceptable gas generating agent can be about 1.4 weight % of the total dosage form. In other embodiments, the second pharmaceutically acceptable gas generating agent can be about 1.6 weight % of the total dosage form. In certain embodiments, the one or more pharmaceutically acceptable gas generating agents are sodium bicarbonate and citric acid. In some embodiments, the first pharmaceutically acceptable gas generating agent is sodium bicarbonate and the second pharmaceutically acceptable gas generating agent is citric acid.

In certain embodiments, the swellable and/or floating layer can include from about 1.6 weight % to about 2.3 weight % of a binder based on the total weight of the dosage form. In certain embodiments, the swellable and/or floating layer can include from about 1.8 weight % to about 2.1 weight % of the binder based on the total weight of the dosage form. In certain embodiments, the swellable and/or floating layer can include about 1.8 weight % of the binder based on the total weight of the dosage form. In certain embodiments, the swellable and/or floating layer can include about 2.1 weight % of the binder based on the total weight of the dosage form. In certain embodiments, the binder can be Povidone K30.

In certain embodiments, the swellable and/or floating layer can include from about 0.3 to about 1.3 weight % of the one or more pharmaceutically acceptable lubricants based on the total weight of the dosage form. In certain embodiments, the swellable and/or floating layer can include from about 0.4 to about 1.2 weight % of the one or more pharmaceutically acceptable lubricants based on the total weight of the dosage form. In certain embodiments, the swellable and/or floating layer can include from about 0.7 to about 0.9 weight % of the one or more pharmaceutically acceptable lubricants based on the total weight of the dosage form. In certain embodiments, the one or pharmaceutically acceptable lubricants can be selected from magnesium stearate, colloidal silicon dioxide, and combinations thereof. In certain embodiments, the controlled release doxycycline layer can include from about 0.4 weight % colloidal silicon dioxide and about 0.4 weight % magnesium stearate, based on the total weight of the dosage form.

The expandable porous coating can include one or more hydrophobic release controlling agents, optionally hydrophilic release controlling agents, one or more plasticizers, and one or more pharmaceutically acceptable lubricants. In one embodiment, the hydrophobic release controlling agent can be present in an amount of from about 1 weight % to about 3 weight % based on the total weight of the dosage form. In another embodiment, the hydrophobic release controlling agent can be present in an amount of from about 1.3 weight % to about 2.5 weight % based on the total weight of the dosage form. In another embodiment, the hydrophobic release controlling agent can be present in an amount of from about 1.3 weight % to about 2.5 weight % based on the total weight of the dosage form. In another embodiment, the hydrophobic release controlling agent can be present in an amount of from about 1.6 weight % to about 2.3 weight % based on the total weight of the dosage form. In another embodiment, the hydrophobic release controlling agent can be present in about 1.6 weight % based on the total weight of the dosage form. In another embodiment, the hydrophobic release controlling agent can be present in about 2.3 weight % based on the total weight of the dosage form. In certain embodiments, the hydrophobic release controlling agent can be a copolymer of methyl or ethyl acrylate, methyl methacrylate, and a methacrylic acid ester having a quaternary amine present. In particular embodiments, the copolymer of methyl or ethyl acrylate, methyl methacrylate, and a methacrylic acid ester having a quaternary amine present can be EUDRAGIT® RL PO manufactured by Evonik.

In certain embodiments, the expandable porous coating can optionally include from about 0.3 weight % to about 0.7 weight % of a hydrophilic release controlling agent based on the total weight of the dosage form. In certain embodiments, the expandable porous coating can optionally include from about 0.4 weight % to about 0.6 weight % of the hydrophilic release controlling agent based on the total weight of the dosage form. In certain embodiments, the expandable porous coating can optionally include about 0.5 weight % of the hydrophilic release controlling agent based on the total weight of the dosage form. In certain embodiments, the hydrophilic release controlling agent can be hypromellose.

In certain embodiments, the expandable porous coating can include one or more plasticizers in an amount from about 0.1 weight % to about 0.7 weight % based on the total weight of the dosage form. In certain embodiments, the expandable porous coating can include one or more plasticizers in an amount from about 0.2 weight % to about 0.6 weight % based on the total weight of the dosage form. In certain embodiments, the expandable porous coating can include one or more plasticizers in an amount from about 0.3 weight % to about 0.5 weight % based on the total weight of the dosage form. In certain embodiments, the expandable porous coating can include one or more plasticizers at about 0.3 weight % or about 0.5 weight % based on the total weight of the dosage form. In certain embodiments, the plasticizer can be triethyl citrate or polyethylene glycol 6000.

In certain embodiments, the expandable porous coating can include the pharmaceutically acceptable lubricant in an amount from about 0.1 weight % to about 0.5 weight % based on the total weight of the dosage form. In certain embodiments, the expandable porous coating can include the pharmaceutically acceptable lubricant in an amount from about 0.2 weight % to about 0.4 weight % based on the total weight of the dosage form. In certain embodiments, the expandable porous coating can include the pharmaceutically acceptable lubricant in an amount from about 0.2 weight % to about 0.3 weight % based on the total weight of the dosage form. In certain embodiments, the expandable porous coating can include the pharmaceutically acceptable lubricant at about 0.3 weight % or about 0.2 weight % based on the total weight of the dosage form. In certain embodiments, the lubricant is talc.

In certain embodiments, the seal coating can include a hydrophilic release controlling agent and a plasticizer. In certain embodiments, the seal coating can include from about 1.3 weight % to about 2.1 weight % of the hydrophilic release controlling agent based on the total weight of the dosage form. In certain embodiments, the seal coating can include from about 1.5 weight % to about 1.9 weight % of the hydrophilic release controlling agent based on the total weight of the dosage form. In certain embodiments, the seal coating can include about 1.7 weight % of the hydrophilic release controlling agent based on the total weight of the dosage form. In certain embodiments, the hydrophilic release controlling agent can be hypromellose E5. In certain embodiments, the seal coating can include a plasticizer in an amount from about 0.01 weight % to about 0.5 weight % based on the total weight of the dosage form. In certain embodiments, the seal coating can include a plasticizer in an amount from about 0.05 weight % to about 0.4 weight % based on the total weight of the dosage form. In certain embodiments, the seal coating can include a plasticizer in an amount from about 0.1 weight % to about 0.3 weight % based on the total weight of the dosage form. In certain embodiments, the seal coating can include one or more plasticizers at about 0.2 weight % based on the total weight of the dosage form. In certain embodiments, the plasticizer can be triethyl citrate or polyethylene glycol 6000.

In certain embodiments, the immediate release doxycycline overcoat can include from about 0.5 to about 3.2 weight % doxycycline based on the total weight of the dosage form, from about 1 to about 2.7 weight % doxycycline based on the total weight of the dosage form, from about 1.5 to about 2.2% doxycycline based on the total weight of the dosage form, or about 1.6 weight % doxycycline based on the total weight of the dosage form.

In certain embodiments, the immediate release doxycycline overcoat can include from about 0.1 weight % to about 4 weight % of a hydrophilic release controlling agent based on the total weight of the dosage form, from about 1 weight % to about 3 weight % of the hydrophilic release controlling agent based on the total weight of the dosage form, or about 2 weight % of the hydrophilic release controlling agent based on the total weight of the dosage form. In certain embodiments, the immediate release doxycycline overcoat can include about 2.1 or 2.2 weight % hydrophilic release controlling agent based on the total weight of the dosage form. In certain embodiments, the hydrophilic release controlling agent can be hypromellose.

In certain embodiments, the immediate release doxycycline overcoat can include a plasticizer in an amount from about 0.01 weight % to about 0.5 weight % based on the total weight of the dosage form. In certain embodiments, the immediate release doxycycline overcoat can include a plasticizer in an amount from about 0.05 weight % to about 0.4 weight % based on the total weight of the dosage form. In certain embodiments, the immediate release doxycycline overcoat can include a plasticizer in an amount from about 0.1 weight % to about 0.3 weight % based on the total weight of the dosage form. In certain embodiments, the immediate release doxycycline overcoat can include one or more plasticizers at about 0.2 weight % based on the total weight of the dosage form. In certain embodiments, the plasticizer can be triethyl citrate or polyethylene glycol 6000.

Swellable/Semi-permeable Dosage Form

In some embodiments, the controlled release pharmaceutical dosage form can be a swellable/semi-permeable dosage form having a swellable controlled release drug core, a permeable/expandable porous coating, an optional seal coating, and an immediate release doxycycline overcoat.

In certain embodiments, the swellable controlled release drug core can comprise from about 5 to about 15 weight % doxycycline based on the total weight of the dosage form, from about 6 to about 13 weight % doxycycline based on the total weight of the dosage form, from about 7 to about 12% doxycycline based on the total weight of the dosage form, and from about 8 to about 10 weight % doxycycline based on the total weight of the dosage form. In particular embodiments, the swellable controlled release drug core can include from about 9 to about 10 weight % doxycycline based on the total weight of the dosage form, and in certain embodiments about 9 to about 9.8 weight % doxycycline based on the total weight of the dosage form, and in still further embodiments, about 9.7 or about 9.1 weight % doxycycline based on the total weight of the dosage form.

In some embodiments, the swellable controlled release core can further include one or more excipients and/or other formulating agents, such as one or more diluents, one or more pore forming agents, one or more hydrophilic release controlling agents, one or more binders, and one or more lubricants. For example, the swellable controlled release drug core can include from about 40 to about 60 weight % of a first diluent based on the total weight of the dosage form, from about 45 to about 55 weight %, or from about 47 to about 51 weight % based on the total weight of the dosage form. In certain embodiments, the first diluent can comprise about 46 to about 47 weight % based on the total weight of the dosage form. In other embodiments, the first diluent can comprise about 50.5 to about 51.5 weight % based on the total weight of the dosage form.

In some embodiments, the swellable controlled release drug core can include from about 10 to about 20 weight % of a second diluent based on the total weight of the dosage form, from about 12 to about 18 weight %, or from about 15 to about 17 weight % based on the total weight of the dosage form. In certain embodiments, the first diluent can comprise about 16 weight % based on the total weight of the dosage form. In particular embodiments, the first diluent is lactose monohydrate.

In certain embodiments, the swellable controlled release drug core can include from about 2 to about 6 weight % of the pore forming agent based on the total weight of the dosage form. In other embodiments, the swellable controlled release drug core can include from about 3 to about 5 weight % of the pore forming agent based on the total weight of the dosage form. In other embodiments, the pore forming agent can comprise about 4 weight % of the controlled release drug core, based on the total weight of the dosage form.

In certain embodiments, the swellable controlled release drug core can include from about 1 to about 15 weight % of a binder based on the total weight of the dosage form. In other embodiments, the swellable controlled release drug core can include from about 7 to about 11 weight % of the binder based on the total weight of the dosage form. In other embodiments, the swellable controlled release drug core can include from about 9 to about 10 weight % of the binder based on the total weight of the dosage form. In other embodiments, the swellable controlled release drug core can include 9.7 weight % of the binder based on the total weight of the dosage form. In other embodiments, the swellable controlled release drug core can include from about 3 to about 5 weight % of the binder based on the total weight of the dosage form. In other embodiments, the swellable controlled release drug core can include about 4 weight % of the binder based on the total weight of the dosage form. In certain embodiments, the binder is povidone K30.

In certain embodiments, the swellable controlled release drug core can include from about 1 to about 7 weight % of a hydrophilic release controlling agent based on the total weight of the dosage form. In other embodiments, the swellable controlled release drug core can include from about 3 to about 5 weight % of the hydrophilic release controlling agent based on the total weight of the dosage form. In other embodiments, the swellable controlled release drug core can include about 4 weight % of the hydrophilic release controlling agent based on the total weight of the dosage form. In certain embodiments, the hydrophilic release controlling agent is hypromellose.

In certain embodiments, the swellable controlled release drug core can include from about 1 to about 5 weight % of a first and second lubricant based on the total weight of the dosage form. In other embodiments, the swellable controlled release drug core can include from about 1 to about 3 weight % of the first and second lubricants based on the total weight of the dosage form. In other embodiments, the swellable controlled release drug core can include from about 1 to about 2 weight % of the first and second lubricants based on the total weight of the dosage form. In other embodiments, the swellable controlled release drug core can include from about 1 to about 1.5 weight % of the first and second lubricants based on the total weight of the dosage form. In some embodiments, the first lubricant can be colloidal silicon dioxide. In some embodiments the second lubricant can be magnesium stearate.

The permeable/expandable porous coating can comprise one or more hydrophobic release controlling agents, at least one plasticizers, and at least one lubricant. In certain embodiments, the one or more hydrophobic release controlling agents can comprise from about 0.1 to about 5 weight % of the permeable/expandable porous coating based on the total weight of the dosage form. In other embodiments, the one or more hydrophobic release controlling agents can comprise from about 2 to about 4 weight % of the permeable/expandable porous coating based on the total weight of the dosage form. In other embodiments, the one or more hydrophobic release controlling agents can comprise from about 2 to about 3 weight % of the permeable/expandable porous coating based on the total weight of the dosage form. In other embodiments, the one or more hydrophobic release controlling agents can comprise from about 2.5 to about 3 weight % of the permeable/expandable porous coating based on the total weight of the dosage form. In some embodiments the one or more hydrophobic release controlling agents can comprise a first hydrophobic release controlling agent and a second hydrophobic release controlling agent. In some embodiments, the first hydrophobic release controlling agent can comprise from about 2 to about 4 weight % of the permeable/expandable porous coating based on the total weight of the dosage form. In other embodiments the first hydrophobic release controlling agent can comprise about 2.1 or about 2.3 weight % of the permeable/expandable porous coating based on the total weight of the dosage form. In some embodiments, the second hydrophobic release controlling agent can comprise from about 0.1 to about 0.8 weight % of the permeable/expandable porous coating based on the total weight of the dosage form. In other embodiments the second hydrophobic release controlling agent can comprise about 0.5 or about 0.4 weight % of the permeable/expandable porous coating based on the total weight of the dosage form. In some embodiments, the one or more hydrophobic release controlling agents can be a copolymer of methyl or ethyl acrylate, methyl methacrylate, and a methacrylic acid ester having a quaternary amine present. In particular embodiments, the copolymer of copolymer of methyl or ethyl acrylate, methyl methacrylate, and a methacrylic acid ester having a quaternary amine present can be EUDRAGIT®. In particular embodiments, the EUDRAGIT® can be EUDRAGIT® RL PO, EUDRAGIT® RS PO, or any combination thereof. In some embodiments, the first hydrophobic release controlling agent can be EUDRAGIT® RL PO. In some embodiments, the second hydrophobic release controlling agent can be EUDRAGIT® RS PO.

In certain embodiments, the seal coating can include a hydrophilic release controlling agent and a plasticizer. In certain embodiments, the seal coating can include from about 1.3 weight % to about 2.1 weight % of the hydrophilic release controlling agent based on the total weight of the dosage form. In certain embodiments, the seal coating can include from about 1.5 weight % to about 1.9 weight % of the hydrophilic release controlling agent based on the total weight of the dosage form. In certain embodiments, the seal coating can include about 1.6 or about 1.7 weight % of the hydrophilic release controlling agent based on the total weight of the dosage form. In certain embodiments, the hydrophilic release controlling agent can be hypromellose. In certain embodiments, the seal coating can include a plasticizer in an amount from about 0.01 weight % to about 0.5 weight % based on the total weight of the dosage form. In certain embodiments, the seal coating can include a plasticizer in an amount from about 0.05 weight % to about 0.4 weight % based on the total weight of the dosage form. In certain embodiments, the seal coating can include a plasticizer in an amount from about 0.1 weight % to about 0.3 weight % based on the total weight of the dosage form. In certain embodiments, the seal coating can include one or more plasticizers at about 0.2 weight % based on the total weight of the dosage form. In certain embodiments, the plasticizer can be triethyl citrate or polyethylene glycol 6000.

In certain embodiments, the immediate release doxycycline overcoat can include from about 0.5 to about 3.2 weight % doxycycline based on the total weight of the dosage form, from about 1 to about 2.7 weight % doxycycline based on the total weight of the dosage form, from about 1 to about 2% doxycycline based on the total weight of the dosage form, and in certain embodiments about 1.1 or about 1.6 weight % doxycycline based on the total weight of the dosage form.

In certain embodiments, the immediate release doxycycline overcoat can include from about 0.1 weight % to about 4 weight % of a hydrophilic release controlling agent based on the total weight of the dosage form, from about 1 weight % to about 3 weight % of the hydrophilic release controlling agent based on the total weight of the dosage form, or from about 1.5 weight % to about 2.3 weight % of the hydrophilic release controlling agent based on the total weight of the dosage form. In certain embodiments, the immediate release doxycycline overcoat can include about 1.7 or 2.1 weight % hydrophilic release controlling agent based on the total weight of the dosage form. In certain embodiments, the hydrophilic release controlling agent can be hypromellose.

In certain embodiments, the immediate release doxycycline overcoat can include a plasticizer in an amount from about 0.01 weight % to about 0.5 weight % based on the total weight of the dosage form. In certain embodiments, the immediate release doxycycline overcoat can include a plasticizer in an amount from about 0.05 weight % to about 0.4 weight % based on the total weight of the dosage form. In certain embodiments, the immediate release doxycycline overcoat can include a plasticizer in an amount from about 0.2 weight % to about 0.4 weight % based on the total weight of the dosage form. In certain embodiments, the immediate release doxycycline overcoat can include one or more plasticizers at about 0.2 or about 0.4 weight % based on the total weight of the dosage form. In certain embodiments, the plasticizer is triethyl citrate or polyethylene glycol 6000.

Gastroretentive/Bioadhesive Matrix Dosage Form

In certain embodiments, the controlled release pharmaceutical dosage form can comprise a controlled release layer, an inert swellable/bioadhesive layer, and an immediate release doxycycline overcoat.

In certain embodiments, the controlled release layer can comprise doxycycline, one or more diluents, one or more hydrophilic release controlling agents, and one or more lubricants.

In certain embodiments, the controlled release layer can comprise from about 5 to about 15 weight % doxycycline based on the total weight of the dosage form, from about 6 to about 13 weight % doxycycline based on the total weight of the dosage form, from about 7 to about 12% doxycycline based on the total weight of the dosage form, and in certain embodiments from about 8 to about 10 weight % doxycycline based on the total weight of the dosage form. In particular embodiments, the swellable controlled release drug core can include from about 9 to about 10 weight % doxycycline based on the total weight of the dosage form, and in certain embodiments about 10.2 weight % doxycycline based on the total weight of the dosage form.

In certain embodiments, the controlled release layer can comprise a first and a second diluent. In certain embodiments, the first diluent can comprise from about 10 to about 20 weight % of the controlled release layer based on the total weight of the dosage form. In other embodiments, the first diluent can comprise about 15 to about 16 weight % of the controlled release layer based on the total weight of the dosage form. In other embodiments, the first diluent can comprise about 15.5 weight % of the controlled release layer based on the total weight of the dosage form. In some embodiments, the first diluent can be microcrystalline cellulose. In certain embodiments, the second diluent can comprise from about 10 to about 20 weight % of the controlled release layer based on the total weight of the dosage form. In other embodiments, the second diluent can comprise about 14 to about 15 weight % of the controlled release layer based on the total weight of the dosage form. In other embodiments, the second diluent can comprise about 14.6 weight % of the controlled release layer based on the total weight of the dosage form. In some embodiments, the second diluent can be mannitol.

In certain embodiments, the controlled release layer can comprise from about 1 to about 15 weight % of the hydrophilic release controlling agent based on the total weight of the dosage form. In other embodiments, the controlled release layer can include from about 5 to about 10 weight % of the hydrophilic release controlling agent based on the total weight of the dosage form. In other embodiments, the controlled release layer can include from about 7 to about 8 weight % of the first hydrophilic release controlling agent based on the total weight of the dosage form. In other embodiments, the controlled release layer can include 7.3 weight % of the hydrophilic release controlling agent based on the total weight of the dosage form. In particular embodiments the hydrophilic release controlling agent is hypromellose.

In certain embodiments, the controlled release layer can comprise one or more lubricants. In particular embodiments, the controlled release layer can comprise a first lubricant and a second lubricant. In some embodiments, the first lubricant can comprise from about 0.01 to about 1 weight % of the controlled release layer based on the total weight of the dosage form. In other embodiments, the first lubricant can comprise from about 0.1 to about 1 weight % of the controlled release layer based on the total weight of the dosage form. In other embodiments, the first lubricant can comprise from about 0.3 to about 0.7 weight % of the controlled release layer based on the total weight of the dosage form. In still other embodiments, the first lubricant can comprise about 0.5 weight % of the controlled release layer based on the total weight of the dosage form. In particular embodiments, the first lubricant can be colloidal silicon dioxide. In some embodiments, the second lubricant can comprise from about 0.01 to about 1 weight % of the controlled release layer based on the total weight of the dosage form. In other embodiments, the second lubricant can comprise from about 0.1 to about 1 weight % of the controlled release layer based on the total weight of the dosage form. In other embodiments, the second lubricant can comprise from about 0.2 to about 0.6 weight % of the controlled release layer based on the total weight of the dosage form. In still other embodiments, the second lubricant can comprise about 0.4 weight % of the controlled release layer based on the total weight of the dosage form. In particular embodiments, the second lubricant can be magnesium stearate.

In certain embodiments, the inert swellable/bioadhesive layer can comprise one or more hydrophilic release controlling agents, one or more swelling agents, one or more diluents, and one or more lubricants.

In particular embodiments, the inert swellable/bioadhesive layer can comprise a first and a second hydrophilic release controlling agent. In certain embodiments, the swellable/bioadhesive layer can comprise from about 5 to about 25 weight % of the first hydrophilic release controlling agent based on the total weight of the dosage form. In other embodiments, the swellable/bioadhesive layer can include from about 5 to about 15 weight % of the first hydrophilic release controlling agent based on the total weight of the dosage form. In other embodiments, the swellable/bioadhesive layer can include from about 9 to about 13 weight % of the first hydrophilic release controlling agent based on the total weight of the dosage form. In other embodiments, the swellable/bioadhesive layer can include about 11 weight % of the first hydrophilic release controlling agent based on the total weight of the dosage form. In certain embodiments, the first hydrophilic release controlling agent can be hypromellose.

In certain embodiments, the swellable/bioadhesive layer can comprise from about 5 to about 25 weight % of the second hydrophilic release controlling agent based on the total weight of the dosage form. In other embodiments, the swellable/bioadhesive layer can include from about 5 to about 15 weight % of the second hydrophilic release controlling agent based on the total weight of the dosage form. In other embodiments, the swellable/bioadhesive layer can include from about 9 to about 13 weight % of the second hydrophilic release controlling agent based on the total weight of the dosage form. In other embodiments, the swellable/bioadhesive layer can include about 11 weight % of the second hydrophilic release controlling agent based on the total weight of the dosage form. In certain embodiments, the second hydrophilic release controlling agent can be polyethylene oxide.

In certain embodiments, the swellable/bioadhesive layer can include about 1 to about 10 weight % of a third hydrophilic release controlling agent based on the total weight of the dosage form. In other embodiments, the swellable/bioadhesive layer can include about 2 to about 6 weight % of the third hydrophilic release controlling agent based on the total weight of the dosage form. In other embodiments, the swellable/bioadhesive layer can include about 4 to about 5 weight % of the third hydrophilic release controlling agent based on the total weight of the dosage form. In other embodiments, the swellable/bioadhesive layer can include about 4.3 weight % of the third hydrophilic release controlling agent based on the total weight of the dosage form. In certain embodiments, the third hydrophilic release controlling agent is a carbomer. In particular embodiments, the carbomer can be Carbopol 974P. In some embodiments, the third hydrophilic release controlling agent can also act as a swelling agent.

In certain embodiments, the one or more swelling agents can comprise a first and second swelling agent. In certain embodiments, the swellable/bioadhesive layer can comprise about 1 to about 10 weight % of the first swelling agent based on the total weight of the dosage form. In other embodiments, the swellable/bioadhesive layer can include about 4 to about 6 weight % of the first swelling agent based on the total weight of the dosage form. In other embodiments, the swellable/bioadhesive layer can include about 5 to about 6 weight % of the swelling agent based on the total weight of the dosage form. In other embodiments, the swellable/bioadhesive layer can include about 5.4 weight % of the first swelling agent based on the total weight of the dosage form. In certain embodiments, the first swelling agent can be partially pregelatinized starch. In certain embodiments, the swellable/bioadhesive layer can comprise about 1 to about 10 weight % of the second swelling agent based on the total weight of the dosage form. In other embodiments, the swellable/bioadhesive layer can include about 4 to about 6 weight % of the second swelling agent based on the total weight of the dosage form. In other embodiments, the swellable/bioadhesive layer can include about 5 to about 6 weight % of the second swelling agent based on the total weight of the dosage form. In other embodiments, the swellable/bioadhesive layer can include about 5.4 weight % of the second swelling agent based on the total weight of the dosage form. In certain embodiments, the second swelling agent can be sodium starch glycolate.

In certain embodiments, the one or more lubricants can comprise a first and second lubricant. In certain embodiments, the swellable/bioadhesive layer can comprise about 0.01 to about 1 weight % of the first lubricant based on the total weight of the dosage form. In other embodiments, the swellable/bioadhesive layer can include about 0.1 to about 1 weight % of the first lubricant based on the total weight of the dosage form. In other embodiments, the swellable/bioadhesive layer can include about 0.4 to about 0.6 weight % of the first lubricant based on the total weight of the dosage form. In other embodiments, the swellable/bioadhesive layer can include about 0.5 weight % of the first lubricant based on the total weight of the dosage form. In certain embodiments, the first lubricant can be partially colloidal silicon dioxide. In certain embodiments, the swellable/bioadhesive layer can comprise about 0.01 to about 1 weight % of the second lubricant based on the total weight of the dosage form. In other embodiments, the swellable/bioadhesive layer can include about 0.1 to about 1 weight % of the second lubricant based on the total weight of the dosage form. In other embodiments, the swellable/bioadhesive layer can include about 0.5 to about 0.7 weight % of the second lubricant based on the total weight of the dosage form. In other embodiments, the swellable/bioadhesive layer can include about 0.6 weight % of the second lubricant based on the total weight of the dosage form. In certain embodiments, the second lubricant can be magnesium stearate.

In certain embodiments, the swellable/bioadhesive layer can include about 1 to about 20 weight % of the diluent based on the total weight of the dosage form. In other embodiments, the swellable/bioadhesive layer can include about 5 to about 15 weight % of the diluent based on the total weight of the dosage form. In other embodiments, the swellable/bioadhesive layer can include about 8 to about 12 weight % of the diluent based on the total weight of the dosage form. In other embodiments, the swellable/bioadhesive layer can include about 10 weight % of the diluent based on the total weight of the dosage form. In particular embodiments, the diluent can be mannitol.

In certain embodiments, the immediate release doxycycline overcoat can comprise doxycycline, one or more hydrophilic release controlling agents, and one or more plasticizers.

In certain embodiments, the immediate release doxycycline overcoat can include from about 0.5 to about 3.2 weight % doxycycline based on the total weight of the dosage form, from about 1 to about 2.7 weight % doxycycline based on the total weight of the dosage form, from about 1 to about 2% doxycycline based on the total weight of the dosage form, and in certain embodiments about 1.1 weight % doxycycline based on the total weight of the dosage form.

In certain embodiments, the immediate release doxycycline overcoat can include from about 0.1 weight % to about 4 weight % of a hydrophilic release controlling agent based on the total weight of the dosage form, from about 1 weight % to about 3 weight % of the hydrophilic release controlling agent based on the total weight of the dosage form, or from about 1.3 weight % to about 1.9 weight % of the hydrophilic release controlling agent based on the total weight of the dosage form. In certain embodiments, the immediate release doxycycline overcoat can include about 1.6 weight % hydrophilic release controlling agent based on the total weight of the dosage form. In certain embodiments, the hydrophilic release controlling agent can be hypromellose.

In certain embodiments, the immediate release doxycycline overcoat can include a plasticizer in an amount from about 0.01 weight % to about 0.5 weight % based on the total weight of the dosage form. In certain embodiments, the immediate release doxycycline overcoat can include a plasticizer in an amount from about 0.05 weight % to about 0.4 weight % based on the total weight of the dosage form. In certain embodiments, the immediate release doxycycline overcoat can include a plasticizer in an amount from about 0.2 weight % to about 0.4 weight % based on the total weight of the dosage form. In certain embodiments, the immediate release doxycycline overcoat can include one or more plasticizers at about 0.3 weight % based on the total weight of the dosage form. In certain embodiments, the plasticizer can be triethyl citrate or polyethylene glycol 6000.

The present controlled release pharmaceutical dosage form can be formulated into a tablet prepared using methods known in the art, including wet granulation and direct compression.

In particular embodiments, the controlled release pharmaceutical dosage forms described herein show greater than 90% relative bioavailability when compared with conventional immediate release dosage forms of doxycycline such as MONODOX® 100 mg capsules.

The controlled release pharmaceutical dosage forms described herein can exhibit a mean $C_{max}$ in the range of about 400 to about 1400 ng/ml, and in other embodiments, in the range of about 600 to about 1200 ng/ml, and in certain embodiments, in the range of about 800 to about 1000 ng/ml, measured upon oral administration of a single dose of the dosage form to patients in a fed state. The controlled release pharmaceutical dosage forms can exhibit an area under the plasma concentration versus time curve ("AUC") (0-48 h) in the range of about 13000 to about 21000 ng/ml/h, and in other embodiments, in the range of about 15000 to about 19000 ng/ml/h in as measured upon oral administration of a single dose of the dosage form to patients in a fed state. In still other embodiments, the controlled release pharmaceutical dosage forms can exhibit an AUC (0-96 h) in the range of about 23000 to about 37000 ng/ml/h, or in the range of about 26000 to about 33000 ng/ml/h measured after administration of a single dose of the dosage form to patients in a fed state.

The foregoing examples are illustrative embodiments of the invention and are merely exemplary. A person skilled in the art may make variations and modifications without deviating from the spirit and scope of the invention. All such modifications and variations are intended to be included within the scope of the invention.

EXAMPLES

Example 1

Trilayer Tablets

| | Ingredients | % w/w |
|---|---|---|
| | Immediate release layer | |
| 1 | Doxycycline monohydrate | 3-12 |
| 2 | Lactose monohydrate | 5-45 |
| 3 | Microcrystalline cellulose | 1-40 |
| 4 | Croscarmellose sodium | 1-20 |
| 5 | Povidone | 1-10 |
| 6 | Magnesium stearate | 0.5-3 |
| 7 | Water | q.s |
| | Controlled release layer | |
| 1 | Doxycycline monohydrate | 3-12 |
| 2 | Povidone | 1-5 |
| 3 | Hypromellose | 5-50 |
| 4 | Polyethylene oxide | 0-20 |
| 5 | Microcrystalline cellulose | 5-30 |
| 6 | Magnesium stearate | 1-5 |
| 7 | Water + Isopropyl alcohol | q.s. |
| | Bioadhesive layer | |
| 1 | Polyoxyethylene oxide | 0-25 |
| 2 | Hypromellose | 0-25 |
| 3 | Lactose | 0-15 |
| 4 | Silicon dioxide | 0.5-2 |
| 5 | Magnesium stearate | 0-2 |

Manufacturing Procedure:
Immediate Release Layer

Doxycycline monohydrate was sifted through #30 mesh stainless steel ("SS") sieve along with lactose monohydrate, microcrystalline cellulose, and 50% of the total amount of croscarmellose sodium. The sifted material was then dry mixed in a high shear granulator The above mixture was then granulated with povidone dissolved in water in a high shear rapid mixer granulator. The resulting wet granules were then dried on fluidized bed dryer and sifted through #16 mesh SS sieve. The remaining croscarmellose sodium was then sifted through #30 mesh SS sieve and mixed well with the previously dried and sifted granules. The granules obtained were then lubricated with sifted magnesium stearate that had previously been passed through #40 mesh SS sieve in a Conta blender for 5 mins.

Controlled Release Layer

Doxycycline monohydrate (optionally enteric coated) was sifted through #20 mesh SS sieve with hypromellose and 10% of the total amount of microcrystalline cellulose. The resulting mixture was then granulated with a povidone solution (water-isopropyl alcohol mixture) in a high shear rapid mixer granulator. The wet granules were then dried in fluidized bed dryer and sifted through #16 mesh SS sieve. The dried and sieved granules were then mixed with polyethylene oxide, the remaining quantity of microcrystalline cellulose, and lubricated with magnesium stearate in a Conta blender.

Bioadhesive Layer

Polyethylene oxide and hypromellose were sifted through #30 mesh SS seive. The blend was then lubricated with silicon dioxide and magnesium stearate in a Conta blender.

Final Dosage Form

The lubricated blends of the immediate release layer, the controlled release layer, and the bioadhesive layer were compressed into trilayer tablets of 13.3 mm diameter on a multi-layer tablet compression machine.

Example 2

Enteric Coated Bi-layer System with IR Overcoat

| | Ingredients | % w/w |
|---|---|---|
| | Controlled release layer | |
| 1 | Doxycycline monohydrate | 3-12 |
| 2 | Povidone | 1-5 |
| 3 | Hypromellose | 5-50 |
| 4 | Polyethylene oxide | 0-20 |
| 5 | Microcrystalline cellulose | 5-30 |
| 6 | Magnesium stearate | 1-5 |
| 7 | Water | q.s. |
| | Bioadhesive layer | |
| 1 | Polyoxyethylene oxide | 0-25 |
| 2 | Hypromellose | 0-25 |
| 3 | Lactose | 0-15 |
| 4 | Silicon dioxide | 0.5-2 |
| 5 | Magnesium stearate | 0-2 |
| | Enteric coating | |
| 1 | Eudragit L100-55 | 5-7% |
| 2 | Triethyl citrate | 0.5 |
| 3 | Isopropyl alcohol + Dichloromethane | q.s. |
| | Immediate release outer shell coating (2-15% wt. gain) | |
| 1 | Doxycycline monohydrate | 2-3 |
| 2 | Povidone | 1-40 |
| 3 | Hypromellose | 0.5-35 |
| 4 | Triethyl citrate | 0.5-10 |
| 5 | Titanium dioxide | 0.5-25 |
| 6 | Water + Isopropyl alcohol | q.s. |

Manufacturing Procedure:

Controlled Release Layer

Doxycycline monohydrate, hypromellose, and 10% of the total amount of microcrystalline cellulose were sifted through #20 mesh SS sieve. The resulting mixture was then granulated in an aqueous povidone solution. The resulting wet granules were then dried on a fluidized bed dryer and sifted through #16 mesh SS sieve. The dried sieved granules were then mixed in a Conta blender with polyethylene oxide, the remaining portion of microcrystalline cellulose, and lubricated with magnesium stearate for 5 mins.

Bioadhesive Layer

Polyethylene oxide and hypromellose were mixed and sifted through #20 mesh SS sieve. The resulting blend was the lubricated on a Conta blender with silicon dioxide and magnesium stearate. The lubricated blends of the controlled release layer and the bioadhesive layer were compressed into bilayer tablets of 12.5 mm or 13.3 mm diameter on a double rotary tablet compression machine.

Enteric Coating of Bilayered Tablet

Eudragit L100-55 was dissolved in an isopropyl alcohol and dichloromethane mixture. Triethyl citrate was added to the solution and the resulting mixture was stirred for 15 minutes. Subsequently, the compressed tablets previously prepared were coated with the above solution on a tablet coater until a 3-5% dry weight gain was observed. This produced enteric coated bi-layer tablets.

Immediate Release Outer Shell Coating

A uniform dispersion of povidone and hypromellose was prepared in a water-isopropyl alcohol mixture. Triethyl citrate was added to the dispersion and stirred to mix well. Doxycycline and titanium dioxide were then added to the dispersion and mixed well. The dispersion was then used to coat the enteric coated bi-layer tablets on a tablet coater to obtain a 3-7% dry weight gain.

Example 3

Bioadhesive Bilayer Tablet

| | Ingredients | % w/w |
|---|---|---|
| | Controlled release layer | |
| 1 | Doxycycline monohydrate | 14.3 |
| 2 | Microcrystalline cellulose | 12.8 |
| 3 | Mannitol | 25.0 |
| 4 | Hypromellose K100 LVCR | 7.0 |
| 5 | Povidone K30 | 4.3 |
| 6 | Water | q.s. |
| 7 | Isopropyl alcohol | q.s. |
| 8 | Colloidal silicon dioxide | 0.5 |
| 9 | Magnesium stearate | 0.3 |
| | Bioadhesive layer | |
| 1 | Microcrystalline cellulose | 15.4 |
| 2 | Hypromellose K4MCR | 6.5 |
| 3 | FD&C Blue #1 | 0.1 |
| 4 | Povidone K30 | 1.1 |
| 5 | Polyethylene oxide | 9.1 |
| 6 | Croscarmellose sodium | 3.2 |
| 7 | Colloidal silicon dioxide | 0.2 |
| 8 | Magnesium stearate | 0.2 |
| 9 | Isopropyl alcohol | q.s. |
| 10 | Water | q.s. |

Manufacturing Procedure:

Controlled Release Layer:

Doxycycline monohydrate, hypromellose, mannitol, and microcrystalline cellulose were sifted through #20 mesh SS sieve. Subsequently, the sifted material was dry mixed in a high shear rapid mixer granulator. The resulting mixture was then wet granulated using a povidone solution in an isopropyl alcohol/water mixture. The resulting wet granules were then dried on a fluidized bed dryer and sifted through #18 mesh SS sieve. The dried sifted granules were then lubricated on a Conta blender with colloidal silicon dioxide and magnesium stearate.

Bioadhesive Layer:

Microcrystalline cellulose and hypromellose were sifted through #30 mesh SS sieve and subsequently dry mixed in a high shear rapid mixer granulator. The resulting dry mixture was then wet granulated with a povidone solution (water-isopropyl alcohol mixture). The resulting wet granules were then dried on a fluidized bed dryer and sieved through #16 mesh SS sieve. The dried, sieved material was then mixed with polyethylene oxide, croscarmellose sodium, FD&C Blue #1, and silicon dioxide. The mixture was lubricated on a Conta blender with magnesium stearate.

Final Dosage Form:

Example 4

Bilayer Tablet

| | Ingredients | % w/w |
|---|---|---|
| | Controlled release layer | |
| 1 | Doxycycline monohydrate | 11.5 |
| 2 | Microcrystalline cellulose | 17 |
| 3 | Mannitol | 20 |
| 4 | Polyethylene oxide | 6.8 |
| 5 | Hypromellose K100 LVCR | 6.8 |
| 6 | Povidone K30 | 3.4 |
| 7 | Water | q.s. |
| 8 | Isopropyl alcohol | q.s. |
| 9 | Colloidal silicon dioxide | 0.4 |
| 10 | Magnesium stearate | 0.3 |
| | Immediate release layer | |
| 1 | Doxycycline monohydrate | 2.0 |
| 2 | Microcrystalline cellulose | 13.5 |
| 3 | Mannitol | 13.9 |
| 4 | Sunset Yellow | 0.1 |
| 5 | Povidone K30 | 2.0 |
| 6 | Water | q.s. |
| 7 | Croscarmellose sodium | 1.7 |
| 8 | Colloidal silicon dioxide | 0.3 |
| 9 | Magnesium stearate | 0.3 |

Manufacturing Procedure:

Controlled Release Layer:

Doxycycline monohydrate, hypromellose, polyethylene oxide, mannitol, and microcrystalline cellulose were sieved through #30 mesh SS sieve. The sieved material was then dry mixed in a high shear rapid mixer granulator. The resulting mixture was then wet granulated with a povidone solution (water-isopropyl alcohol mixture). The resulting wet granules were then dried on a fluidized bed dryer and sifted through #16 mesh SS sieve. The dried, sieved material was then lubricated with colloidal silicon dioxide and magnesium stearate on a Conta blender.

Immediate Release Layer:

Doxycycline monohydrate, mannitol, and microcrystalline cellulose were sifted through #30 mesh SS sieve. The sieved material was dry mixed in a high shear rapid mixer granulator and then wet granulated with an aqueous povidone solution. The resulting wet material was then dried on fluidized bed dryer and sifted through #16 mesh SS sieve. The dried, sieved material was then mixed with croscarmellose sodium, sunset yellow, and colloidal silicon dioxide and subsequently lubricated on a Conta blender with magnesium stearate.

Final Dosage Form:

The lubricated blends of the controlled release layer and the immediate release layer were compressed into bilayer tablets of 13.3 mm diameter on a double rotary tablet compression machine.

The lubricated blends of the controlled release layer and the bioadhesive layer were then compressed into bilayer tablets of 13.3 mm diameter on a double rotary tablet compression machine.

Example 5

Extended Release Gastroretentive/Bioadhesive Matrix Technology

| | Ingredients | % w/w |
|---|---|---|
| | A) Controlled release layer | |
| 1 | Doxycycline monohydrate equivalent to 100 mg of Doxycycline | 11.1 |
| 2 | Microcrystalline cellulose | 16.8 |
| 3 | Mannitol | 15.9 |
| 4 | Hypromellose | 7.9 |
| 5 | Water | q.s. |
| 6 | Colloidal silicon dioxide | 0.5 |
| 7 | Magnesium stearate | 0.4 |
| | Proportion of drug CR Layer (% w/w) | 52.6 |
| | B) Inert layer | |
| 1 | Hypromellose | 10.7 |
| 2 | Polyethylene oxide | 10.7 |
| 3 | Carbopol | 4.2 |
| 4 | Partially pregelatinized starch | 5.3 |
| 5 | Sodium starch glycolate | 5.3 |
| 6 | Mannitol | 10.1 |
| 7 | Colloidal silicon dioxide | 0.5 |
| 8 | Magnesium stearate | 0.6 |
| | Proportion of Inert Layer (% w/w) | 47.4 |
| | Total (A + B) | 100.0 |

Final tablets coated with Opadry Yellow for 2-3% weight gain

Manufacturing Procedure:

Controlled Release Layer:

Doxycycline monohydrate, microcrystalline cellulose, hypromellose, and mannitol were sifted through #40 mesh SS sieve and dry mixed for 10 min in a high shear granulator. The resulting mixture was then wet granulated with water in high shear granulator. The wet granules were dried in fluidized bed drier and sifted through #18 mesh SS sieve. Subsequently, colloidal silicon dioxide presifted through a #40 mesh SS sieve was mixed with the dried granules for 10 mins in a Conta blender. The resulting prelubricated mix was then lubricated for 3 minutes with magnesium stearate that had been sifted through a #40 mesh SS sieve to give a controlled release layer blend.

Inert Layer:

Hypromellose, polyethylene oxide, carbopol, partially pregelatinized starch, sodium starch glycolate, mannitol, and colloidal silicon dioxide were weighed and sifted through #40 mesh SS sieve and mixed for 15 minutes. The resulting blend was then compressed into slugs with 22 mm diameter round punches. The slugs were then deslugged in oscillator granulator and the resultant granules were sifted through a #20 SS sieve. The deslugged and sifted granules were then lubricated for 3 mins in a Conta blender with magnesium stearate that had been previously sifted through a #40 mesh SS sieve to give an inert layer blend.

Final Dosage Form:

The controlled release layer blend and the inert layer blend were compressed into bilayer tablets having a diameter of 13.3 mm on a double rotary tablet compression machine. The bilayer tablets were then film coated on a tablet coater using an Opadry dispersion until a 2-3% dry weight gain was observed.

Example 6

Extended Release Polymer Coated Floating Reservoir Technology

| | Ingredients | (% w/w) |
|---|---|---|
| | Swellable controlled release drug core | |
| 1 | Doxycycline monohydrate equivalent to Doxycycline | 11.4 |
| 2 | Lactose | 43.6 |
| 3 | Mannitol | 17.1 |
| 4 | Sodium chloride | 4.5 |
| 5 | Povidone K30 | 9.1 |
| 6 | Hypromellose | 9.1 |
| 7 | Colloidal silicon dioxide | 0.9 |
| 8 | Magnesium stearate | 0.9 |
| | Semi-permeable/Expandable Porous Coating | |
| 1 | EUDRAGIT® RL PO | 2.8 |
| 2 | Triethyl citrate or Polyethylene glycol 6000 | 0.6 |
| 3 | Isopropyl alcohol | q.s. |
| 4 | Acetone | q.s. |
| | Total weight | 100.0 |

Manufacturing Procedure:
Swellable Controlled Release Drug Core

Doxycycline monohydrate, lactose, mannitol, sodium chloride, povidone K30 and hypromellose were weighed, sifted through #30 mesh SS sieve, and dry mixed in a blender for 10 min. The resulting mixture was then blended for 3 min with 50% of the total quantity of a mixture of colloidal silicon dioxide and magnesium stearate (each presifted through #40 SS sieve). The resulting blend was then compressed into slugs with 22 mm diameter round punches. The slugs were then deslugged in an oscillator granulator and the resultant granules were sifted through a #20 stainless steel sieve. The deslugged and sifted granules were then mixed with the remaining quantity of colloidal silicon dioxide, previously sifted through a #40 mesh SS sieve, for 5 mins on a Conta blender. The blend was further lubricated with remaining quantity of magnesium stearate, previously sifted through a #40 mesh SS sieve, for 3 mins on a Conta blender. The lubricated blend was then compressed into tablets having a 13.3 mm diameter on a single rotary tablet compression machine.

Semi-Permeable/Expandable Porous Coating

EUDRAGIT® RL PO was dissolved in a 1:1 mixture of isopropyl alcohol and acetone. Triethyl citrate or polyethylene glycol 6000 was added to the EUDRAGIT® solution and the resultant was stirred for 15 minutes to give a clear solution. The previously prepared tablets were then coated with the EUDRAGIT® solution on a tablet coater until a 3 to 4% weight gain on dry weight basis was observed.

Examples 7A and 7B

Extended Release Polymer Coated Floating Reservoir Technology with Loading Dose

| | Ingredients | Example 7A (% w/w) | Example 7B (% w/w) |
|---|---|---|---|
| | Swellable controlled release drug core | | |
| 1 | Doxycycline monohydrate equivalent to Doxycycline | 9.7 | 9.1 |
| 2 | Lactose monohydrate | 46.7 | 51.2 |
| 3 | Mannitol | 16.2 | 16.0 |
| 4 | Sodium chloride | 4.3 | 4.3 |
| 5 | Povidone K30 | 8.7 | 4.3 |
| 6 | Hypromellose | 4.3 | 4.3 |
| 7 | Colloidal silicon dioxide | 1.0 | 1.0 |
| 8 | Magnesium stearate | 1.0 | 0.5 |
| | Permeable/Expandable Porous Coating | | |
| 1 | EUDRAGIT® RL PO | 2.3 | 2.1 |
| 2 | EUDRAGIT® RS PO | 0.5 | 0.4 |
| 3 | Triethyl citrate or Polyethylene glycol 6000 | 0.5 | 0.4 |
| 4 | Talc | — | 0.3 |
| 5 | Isopropyl alcohol | q.s. | q.s. |
| 6 | Acetone | q.s. | q.s. |
| | Seal coating | | |
| 1 | Hypromellose | 1.6 | 1.7 |
| 2 | Triethyl citrate or Polyethylene glycol 6000 | 0.2 | 0.2 |
| 3 | Dichloromethane | q.s. | q.s. |
| 4 | Methanol | q.s. | q.s. |
| | Immediate release overcoating | | |
| 1 | Doxycycline monohydrate equivalent to Doxycycline | 1.1 | 1.7 |
| 2 | Hypromellose | 1.7 | 2.1 |
| 3 | Triethyl citrate or Polyethylene glycol 6000 | 0.2 | 0.4 |
| 4 | Dichloromethane | q.s. | q.s. |
| 5 | Methanol | q.s. | q.s. |
| | Total weight | 100.0 | 100.0 |

Manufacturing Procedure:
Swellable Controlled Release Drug Core

Doxycycline monohydrate, lactose, mannitol, sodium chloride, povidone K30, and hypromellose were weighed, sifted through a #40 mesh SS sieve and dry mixed in a blender for 10 minutes. The resulting mixture was then lubricated for 3 minutes with 50% of the total quantity of a mixture of colloidal silicon dioxide and magnesium stearate that had been previously weighed and sifted through #40 mesh SS sieve. The resulting blend was then compressed into slugs with 24 mm diameter round punches. The slugs were then deslugged in oscillator granulator and the resultant granules were sifted through a #20 stainless steel sieve. The deslugged and sifted granules were then mixed for 5 mins on a Conta blender with remaining quantity of colloidal silicon dioxide previously sifted through a #40 mesh SS sieve. The blend was further lubricated for an additional 3 mins on a Conta blender with the remaining quantity of magnesium stearate previously sifted through a #40 mesh SS sieve. The lubricated blend was then compressed into tablets having a 13.3 mm diameter using a single rotary tablet compression machine.

Permeable/Expandable Porous Coating:

EUDRAGIT® RL PO and RS PO were added to a 1:1 mixture of isopropyl alcohol and acetone and stirred until a clear solution was obtained. Triethyl citrate or polyethylene glycol 6000 was added to the clear solution and the resultant mixture was stirred for 15 minutes to give a clear solution. Talc was added to the solution and stirred well to mix. The previously prepared tablets were then coated with the above solution on a tablet coater until a 3 to 4% weight gain on dry weight basis was observed.

Seal Coating:

Hypromellose was added to 1:1 mixture of dichloromethane and methanol and stirred until a clear solution was obtained. Triethyl citrate or polyethylene glycol 6000 was added to the hypromellose solution and the resultant mixture was stirred for 15 mins to give a seal coat solution. The tablets previously coated with EUDRAGIT® RL PO and RS PO were then coated with the seal coat solution on a tablet coater until a 1.5 to 2% weight gain on dry weight basis was observed. This process resulted in seal coated tablets.

Immediate Release Overcoating:

Doxycycline monohydrate was dissolved in 1:1 mixture of dichloromethane and methanol and stirred until a clear solution was obtained. Hypromellose was subsequently added to the solution and the resultant dispersion was stirred until the solution was once again clear. Finally, triethyl citrate or polyethylene glycol 6000 was added to the solution and the resultant was stirred for 30 minutes to give an immediate release overcoat solution. The seal coated tablets were then coated with the immediate release overcoat solution on a tablet coater until 40 mg (±7.5% w/w) weight gain on dry weight basis was observed.

Example 8

Gastroretentive/Bioadhesive Matrix Technology with Immediate Release Over Coat

| | Ingredients | % w/w |
|---|---|---|
| | A) Controlled release layer | |
| 1 | Doxycycline monohydrate equivalent to 90 mg of Doxycycline | 10.2 |
| 2 | Microcrystalline cellulose | 15.5 |
| 3 | Mannitol | 14.6 |
| 4 | Hypromellose | 7.3 |
| 5 | Water | q.s. |
| 6 | Colloidal silicon dioxide | 0.5 |
| 7 | Magnesium stearate | 0.4 |
| | Proportion of controlled release layer (% w/w) | 48.5 |
| | B) Inert swellable/bioadhesive layer | |
| 1 | Hypromellose | 11.0 |
| 2 | Polyethylene oxide | 11.0 |
| 3 | Carbopol 974 P | 4.3 |
| 4 | Partially pregelatinized starch | 5.4 |
| 5 | Sodium starch glycolate | 5.4 |
| 6 | Mannitol | 10.3 |
| 7 | Colloidal silicon dioxide | 0.5 |
| 8 | Magnesium stearate | 0.6 |
| | Proportion of Inert Layer (% w/w) | 48.5 |
| | Total (A + B) | 97.0 |
| | Immediate release drug overcoating | |
| 1 | Doxycycline monohydrate equivalent to 10 mg of Doxycycline | 1.1 |
| 2 | Hypromellose | 1.6 |
| 3 | Triethyl citrate or Polyethylene glycol 6000 | 0.3 |
| 4 | Dichloromethane | qs |
| 5 | Methanol | qs |
| | Proportion of immediate release overcoat (% w/w) | 3.0 |
| | Total | 100.0 |

Manufacturing Procedure:

Controlled Release Layer Blend:

Doxycycline monohydrate, microcrystalline cellulose, hypromellose, and mannitol were sifted through #40 mesh SS sieve and dry mixed for 10 min in a high shear granulator. The resulting mixture was then wet granulated with water in high shear granulator. The wet granules were dried in a fluidized bed drier and sifted through #18 mesh SS sieve. Subsequently, colloidal silicon dioxide presifted through a #40 mesh SS sieve was mixed with the dried granules for 10 mins in a Conta blender. The resulting prelubricated mix was then lubricated for 3 minutes in a Conta blender with magnesium stearate that had been previously sifted through a #40 mesh SS sieve.

Inert Layer Blend:

Hypromellose, polyethylene oxide, carbopol 974 P, partially pregelatinized starch, sodium starch glycolate, mannitol, and colloidal silicon dioxide were weighed, sifted through #40 mesh SS sieve, and subsequently mixed for 15 minutes. The resulting blend was then compressed into slugs with 22 mm diameter round punches. The slugs were then deslugged in oscillator granulator and the resultant granules were sifted through a #20 mesh SS sieve. The deslugged and sifted granules was then lubricated for 3 mins on a Conta blender with magnesium stearate previously sifted through a #40 mesh SS sieve.

Bilayer Core:

The controlled release layer blend and inert layer blend were then compressed into bilayer tablets of 13.3 mm diameter using a double rotary tablet compression machine.

Immediate Release Drug Over Coating:

Hypromellose and triethyl citrate or polyethylene glycol 6000 were weighed and dissolved in a 1:1 mixture of dichloromethane and methanol with continuous stirring until a clear solution was obtained. Subsequently, doxycycline monohydrate was weighed and added to the dichloromethane/methanol solution. The bilayer cores obtained previously were then coated with the above solution on a tablet coater until 29 mg (±7.5% w/w) weight gain on dry weight basis was observed.

Examples 9 & 10

Floating Gastroretentive Extended Release Reservoir Technology Using Gas Generating Agents

| | | Composition % w/w | |
|---|---|---|---|
| | Ingredients | Example 9 | Example 10 |
| | CR drug layer | | |
| 1 | Doxycycline monohydrate equivalent to 85 mg Doxycycline | 9.1 | 9.1 |
| 2 | Lactose monohydrate | 17.7 | 22.4 |
| 3 | Mannitol | 10.7 | 18.7 |
| 4 | Sodium chloride | 4.3 | 4.3 |
| 5 | Hypromellose | 7.5 | — |
| 6 | Povidone K30 | 3.2 | 3.2 |
| 8 | Isopropyl alcohol | q.s. | q.s. |
| 9 | Water | q.s. | q.s. |
| 10 | Colloidal silicon dioxide | 0.5 | 0.5 |
| 11 | Magnesium stearate | 0.5 | 0.5 |
| | Swellable Gas-generating/Floating Layer | | |
| 1 | Polyethylene oxide | 5.4 | 4.6 |
| 2 | Hypromellose | 10.7 | 9.2 |
| 3 | Lactose monohydrate | 12.1 | 10.3 |
| 4 | Sodium bicarbonate | 4.8 | 4.2 |
| 5 | Citric acid | 1.6 | 1.4 |
| 6 | Povidone k30 | 2.1 | 1.8 |

-continued

|   | Ingredients | Example 9 | Example 10 |
|---|---|---|---|
| 7 | Colloidal silicon dioxide | 0.4 | 0.3 |
| 8 | Magnesium stearate | 0.4 | 0.3 |
|   | Permeable/Expandable Porous Coating | | |
| 1 | Eudragit RLPO | 2.4 | 2.4 |
| 2 | Hypromellose | — | 0.5 |
| 3 | Triethyl citrate or polyethylene glycol | 0.5 | 0.4 |
| 3 | Talc | 0.3 | 0.4 |
| 4 | Isopropyl alcohol | q.s. | q.s. |
| 5 | Acetone | q.s. | q.s. |
|   | Seal coating | | |
| 1 | Hypromellose | 1.7 | 1.3 |
| 2 | Triethyl citrate or polyethylene glycol | 0.2 | 0.1 |
| 3 | Dichloromethane | q.s. | q.s. |
| 4 | Methanol | q.s. | q.s. |
|   | IR drug over-coating | | |
| 1 | Doxycycline monohydrate equivalent to 15 mg Doxycycline | 1.6 | 1.6 |
| 2 | Hypromellose | 2.1 | 2.1 |
| 3 | Triethyl citrate or polyethylene glycol 6000 | 0.2 | 0.4 |
| 4 | Dichloromethane | q.s. | q.s. |
| 5 | Methanol | q.s. | q.s. |
|   | Total | 100 | 100 |

Manufacturing Procedure:
Controlled Release Doxycycline Layer Blend:

Doxycycline monohydrate, lactose monohydrate, mannitol, sodium chloride, and hypromellose were weighed and sifted through #20 mesh SS sieve. The sifted materials were then dry mixed in a high shear granulator for 10 minutes. The resultant mixture was then wet granulated with a povidone solution prepared in 60:40% w/w mixture of isopropyl alcohol and water. The resulting granules were dried in a fluidized bed drier and sifted through #20 mesh SS sieve. The resulting dry granules were then mixed for 5 min on a Conta blender with colloidal silicon dioxide that had been previously sifted through a #40 mesh SS sieve. The blend was further lubricated for 3 min on a Conta blender with magnesium stearate that had been previously sifted through a #40 mesh SS sieve.

Floating Layer Blend:

Hypromellose, lactose monohydrate, sodium bicarbonate, citric acid, povidone, polyethylene oxide, and colloidal silicon dioxide were weighed, sifted through #30 mesh SS sieve. All the ingredients were dry mixed in a Conta blender for 10 minutes. The resulting mixture was then lubricated for 3 minutes with magnesium stearate that had been previously sifted through a #40 mesh SS sieve.

Bilayer Tablets:

The controlled release doxycycline layer blend and floating layer blend were then compressed into bilayer tablets of 13.3 mm diameter on a double rotary tablet compression machine.

Permeable/Expandable Porous Coating:

EUDRAGIT® RL PO was added to a 1:1 mixture of isopropyl alcohol and acetone and stirred until a clear solution was obtained. Triethyl citrate or polyethylene glycol 6000 was added to the clear solution and the resultant was stirred for 15 minutes to give a clear solution. Subsequently talc was added to the solution forming a talc dispersion. The previously prepared bilayer tablets were then coated with the talc dispersion using a tablet coater until a 3 to 4% weight gain on dry weight basis was observed.

Seal Coating:

Hypromellose was added to 1:1 mixture of dichloromethane and methanol and stirred until a clear solution was obtained. Triethyl citrate or polyethylene glycol 6000 was added to the hypromellose solution and the resultant was stirred for 15 minutes. The tablets previously coated with EUDRAGIT® RL PO were then coated with the above solution on a tablet coater until 1.5 to 2% weight gain on dry weight basis was observed.

Immediate Release Drug Overcoating:

Doxycycline monohydrate was dissolved in 1:1 mixture of dichloromethane and methanol and stirred until a clear solution was obtained. Hypromellose was subsequently added to the solution and the resultant dispersion was stirred until the solution was once again clear. Finally, triethyl citrate or polyethylene glycol 6000 was added to the solution and the resultant was stirred for 30 minutes. The previously obtained seal coated tablets were then coated with the above solution on a tablet coater until 40 mg (±7.5% w/w) weight gain on dry weight basis was observed.

Example 11

In Vivo Comparative Pharmacokinetic Study

A randomized, open label, balanced, single center, single dose, parallel, fed-state relative bioavailability study was performed in 8 healthy adult male human volunteers who met all inclusion criteria under standard fed conditions.

This study was carried out to compare the rate and extent of absorption of a single oral dose of the controlled release pharmaceutical dosage forms described in Examples 5, 6, and 7A to the rate and extent of absorption of a single oral dose of commercially available MONODOX® 100 mg capsules. Both test articles were administered under fed conditions.

The results of the study are reported in Table 1 and show that Examples 5, 6, and 7A showed comparable $C_{max}$ to the MONODOX® and more than 90% relative bioavailability as compared to MONODOX® for Examples 5 & 7A. The relative bioavailability was just above 80% as compared to MONODOX® for Example 6.

TABLE 1

Results of in vivo comparative pharmacokinetic study of Examples 5, 6, and 7A

| | Comparison of $C_{max}$ | | Comparison of $AUC_{(0-t)}$ | |
|---|---|---|---|---|
| Treatment | Mean $C_{max}$ (ng/ml) | T/R (%) | $AUC_{(0-48\,h)}$ (ng/ml · h) | T/R (%) |
| Reference (MONODOX ®) | 880.6 | — | 16974.2 | — |
| Example 5 | 912.5 | 103.6 | 15799.4 | 93.1 |
| Example 6 | 864.6 | 98.2 | 14029.2 | 82.7 |
| Example 7A | 945.2 | 107.3 | 16365.9 | 96.4 |

$C_{max}$ = Maximum plasma concentration
$AUC_{(0-t)}$ = Area under the plasma concentration vs time curve from t = 0 hours to t = 48 hours
T/R = Ratio of test and reference expressed as a %

Example 12

In Vivo Comparative Pharmacokinetic Cross-over Study

A randomized, open label, balanced, single center, single dose, cross-over, fed state relative bioavailability study was performed in 8 healthy adult male human volunteers who meet all inclusion under standard fed conditions.

This study was carried out to compare the rate and extent of absorption of a single oral dose of the controlled release pharmaceutical dosage forms described in Examples 7B, 8, 9, and 10 against orally administered commercially available MONODOX® 100 mg capsules. All test articles were administered once daily and dosing was performed under fed conditions. As shown in Table 2 (Examples 7B and 8), Table 3 (Example 9), and Table 4 (Example 10), the results indicate that all four test articles had lower $C_{max}$ values than MONODOX®, but had AUC values that were at least about 93% in comparison to MONODOX®. In the case of Examples 8 and 10, the AUC values were about 97% and 99.9% that of MONODOX®, respectively. Thus, the controlled release pharmaceutical dosage forms described herein were able to provide nearly equivalent AUC values to MONODOX® while maintaining a lower $C_{max}$ than MONODOX®.

TABLE 2

Results of in vivo comparative pharmacokinetic study of Example 7B and 8

| Treatment | Comparison of $C_{max}$ | | Comparison of $AUC_{(0-t)}$ | |
|---|---|---|---|---|
| | Mean $C_{max}$ (ng/ml) | T/R (%) | $AUC_{(0-96\,h)}$ (ng/ml · h) | T/R (%) |
| Reference | 1167.9 | — | 29466.9 | — |
| Example 7B | 1131.3 | 96.9 | 28753.3 | 97.6 |
| Example 8 | 989.7 | 84.7 | 28648.1 | 97.2 |

TABLE 3

Results of in vivo comparative pharmacokinetic study of Example 9

| Treatment | Comparison of $C_{max}$ | | Comparison of $AUC_{(0-t)}$ | | Mean $T_{max}$ (h) |
|---|---|---|---|---|---|
| | Mean $C_{max}$ (ng/ml) | T/R (%) | $AUC_{(0-96\,h)}$ (ng/ml · h) | T/R (%) | |
| Reference | 1048.5 | — | 26578.9 | — | 3.9 |
| Example 9 | 822.5 | 78.4 | 24625.8 | 92.7 | 7.0 |

TABLE 4

Results of in vivo comparative pharmacokinetic study of Example 10

| Treatment | Comparison of $C_{max}$ | | Comparison of $AUC_{(0-t)}$ | | Mean $T_{max}$ (h) |
|---|---|---|---|---|---|
| | Mean $C_{max}$ (ng/ml) | T/R (%) | $AUC_{(0-96\,h)}$ (ng/ml · h) | T/R (%) | |
| Reference | 1042.0 | — | 26741.9 | — | 3.9 |
| Example 10 | 972.4 | 93.2 | 26727.9 | 99.9 | 5.1 |

$C_{max}$ = Maximum plasma concentration
$AUC_{(0-t)}$ = Area under the plasma concentration vs time curve from t = 0 hours to t = 96 hours
T/R = Ratio of test and reference expressed in %

Example 13

Swelling Study

Swelling studies were carried out in USP Type I (Basket method) at 75 RPM in 900 mL 0.1N HCl. The % swelling was calculated based on volume of a cylindrical tablet using the equation:

$$\% \text{ swelling} = \frac{[(\text{Volume at any time } t) - (\text{Initial volume})]}{\text{Initial volume}} \times 100$$

and the initial volume of each of Examples 5 through 10 was calculated using the formula:

$$\text{Volume} = \pi \times \left(\frac{d}{2}\right)^2 \times h$$

where, 'd' was the maximum diameter of the tablet and 'h' was the height of the tablet. The calculations used for this example assume that a standard biconvex tablet can be assumed to have about the same volume as a cylinder of the same diameter. For each of Examples 5 through 10, the initial diameter of the tablets was measured to be about 13.3 mm.

The results of the swelling study are reported in Table 5 below

TABLE 5

Results of swelling study

| | % Swelling | | | | | | |
|---|---|---|---|---|---|---|---|
| Time (min) | Example 5 | Example 6 | Example 7A | Example 7B | Example 8 | Example 9 | Example 10 |
| 0 | 0 | 0 | 0 | 0 | 0 | 0 | 0 |
| 30 | 65 | 112 | 87 | 83 | 53 | 89 | 190 |
| 60 | 90 | 183 | 80 | 80 | 60 | 132 | 291 |
| 90 | 100 | 193 | ND | ND | 58 | 183 | 487 |
| 120 | 122 | ND | ND | ND | ND | ND | ND |

ND: Not determined

The results shown in Table 5 show that compositions described in Examples 5 to 10 all swelled to more than 50% of their original volume within 30 minutes, and in each case to a diameter greater than that of the human pyloric sphincter.

Example 15

Determination of Bioadhesion

Six representative formulations of bioadhesive tablets were prepared for evaluation of bioadhesion strength. The formulations used in the study were as follows:

Formula-F1

| S. No | Ingredients | % w/w |
|---|---|---|
| 1 | Polyethylene oxide | 48.9 |
| 2 | Microcrystalline cellulose | 48.9 |
| 3 | Colloidal silicon dioxide | 1.3 |
| 4 | Magnesium stearate | 0.9 |

Formula-F2

| S. No | Ingredients | % w/w |
|---|---|---|
| 1 | Hypromellose | 48.9 |
| 2 | Microcrystalline cellulose | 48.9 |
| 3 | Colloidal silicon dioxide | 1.3 |
| 4 | Magnesium stearate | 0.9 |

Formula-F3

| S. No | Ingredients | % w/w |
|---|---|---|
| 1 | Polyethylene oxide | 48.9 |
| 2 | Xanthan gum | 48.9 |
| 3 | Colloidal silicon dioxide | 1.3 |
| 4 | Magnesium stearate | 0.9 |

Formula-F4

| S. No | Ingredients | % w/w |
|---|---|---|
| 1 | Xanthan gum | 48.9 |
| 2 | Microcrystalline cellulose | 48.9 |
| 3 | Colloidal silicon dioxide | 1.3 |
| 4 | Magnesium stearate | 0.9 |

Formula-F5

| S. No | Ingredients | % w/w |
|---|---|---|
| 1 | Polyethylene oxide | 48.9 |
| 2 | Sodium CMC | 48.9 |
| 3 | Colloidal silicon dioxide | 1.3 |
| 4 | Magnesium stearate | 0.9 |

Formula-F6

| S. No | Ingredients | % w/w |
|---|---|---|
| 1 | Sodium CMC | 48.9 |
| 2 | Microcrystalline cellulose | 48.9 |
| 3 | Colloidal silicon dioxide | 1.3 |
| 4 | Magnesium stearate | 0.9 |

Tablet Manufacturing Procedure:

Each of Tablets F1 through F6 were prepared according to the following general procedure. Microcrystalline cellulose and polyethylene oxide were sifted through #40 mesh SS sieve and blended in a Conta blender. The blend was lubricated with the mixture of colloidal silicon dioxide and magnesium stearate previously sifted through #40 mesh SS sieve. The lubricated blend was compressed into tablets of 13.3 mm diameter on a single rotary tablet compression machine.

Figure 3:
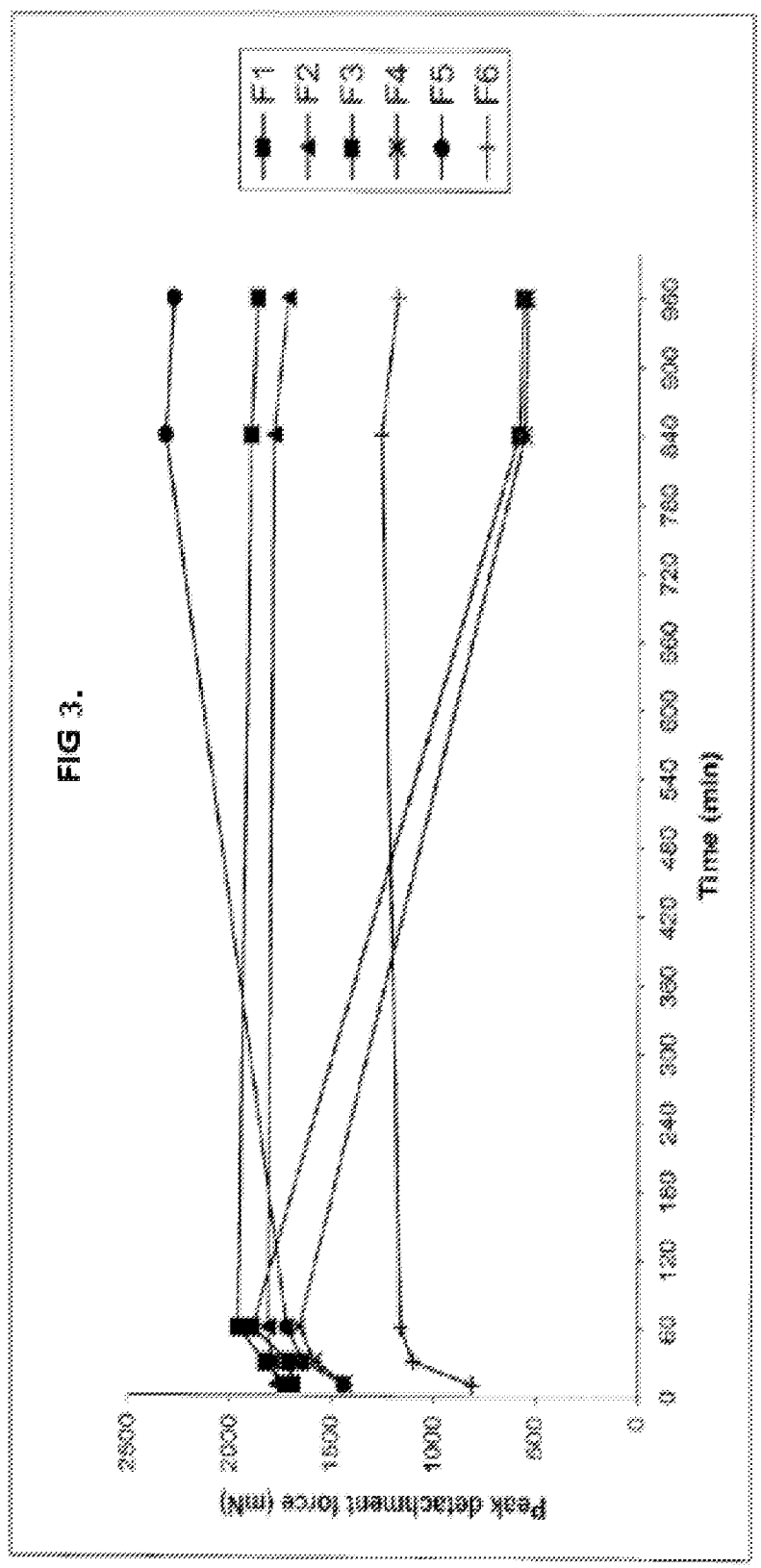
FIG. 3 represents the bioadhesion measurement with peak detachment force as a function of hydration time for bioadhesive tablets F1, F2, F3, F4, F5, and F6.
Figure 4:
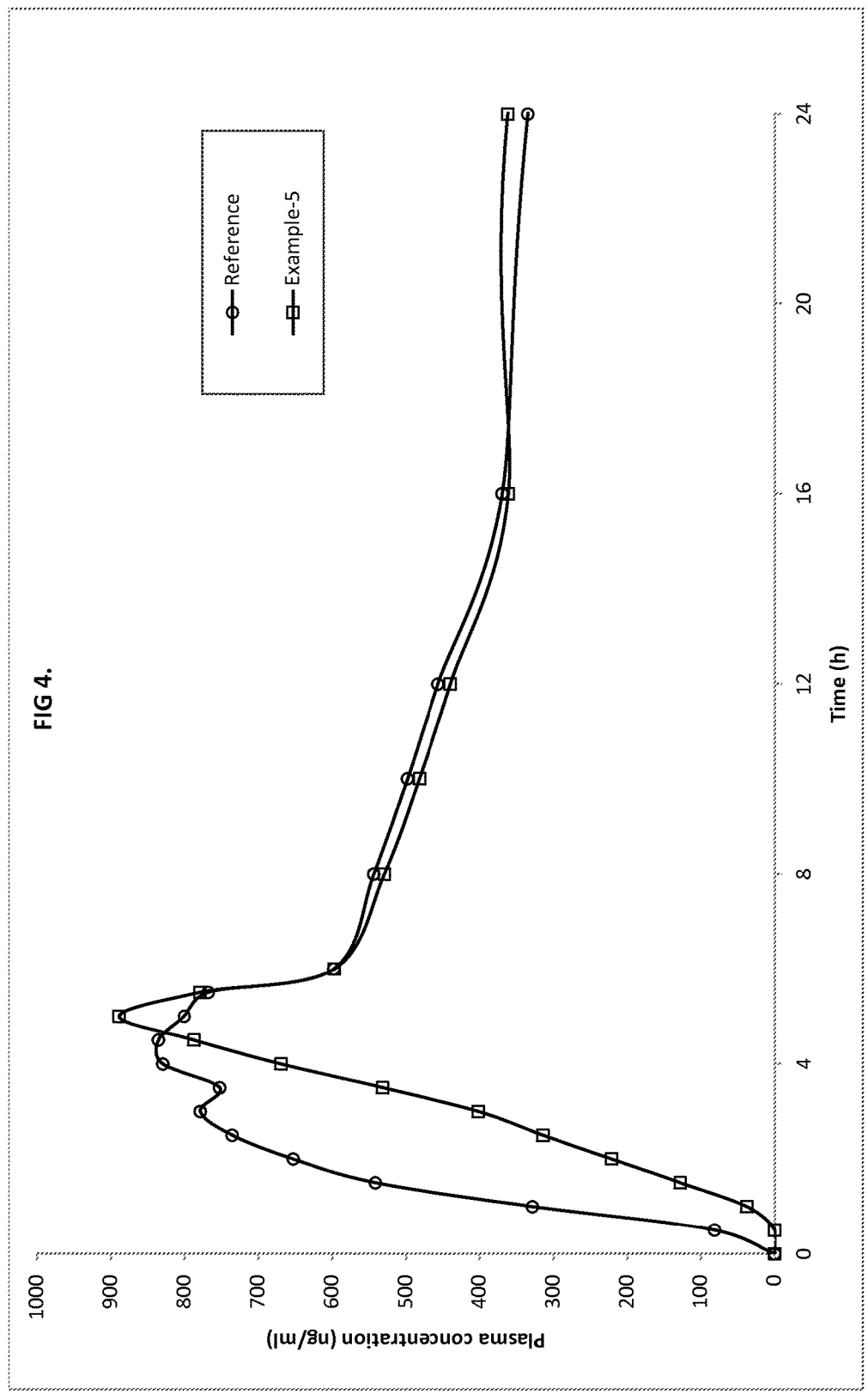
FIG. 4 represents the comparative in vivo pharmacokinetic profiles of controlled release pharmaceutical dosage form of doxycycline described in Example 5 and the reference product as measured in a single dose study.
Figure 6A:
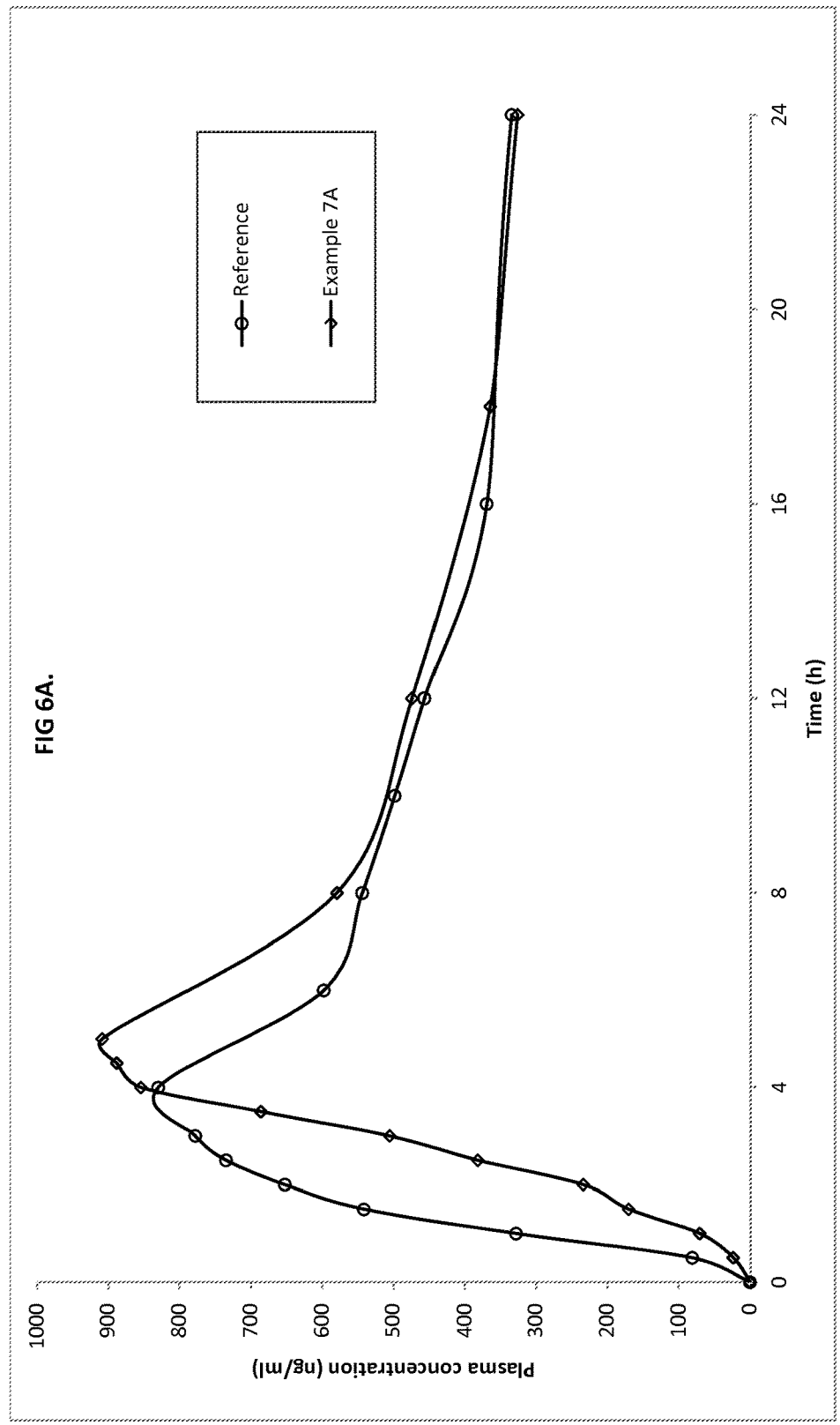
FIG. 6A represents the comparative in vivo pharmacokinetic profiles of controlled release pharmaceutical dosage form of doxycycline described in Example 7A and the reference product as measured in a single dose study.
Figure 7:
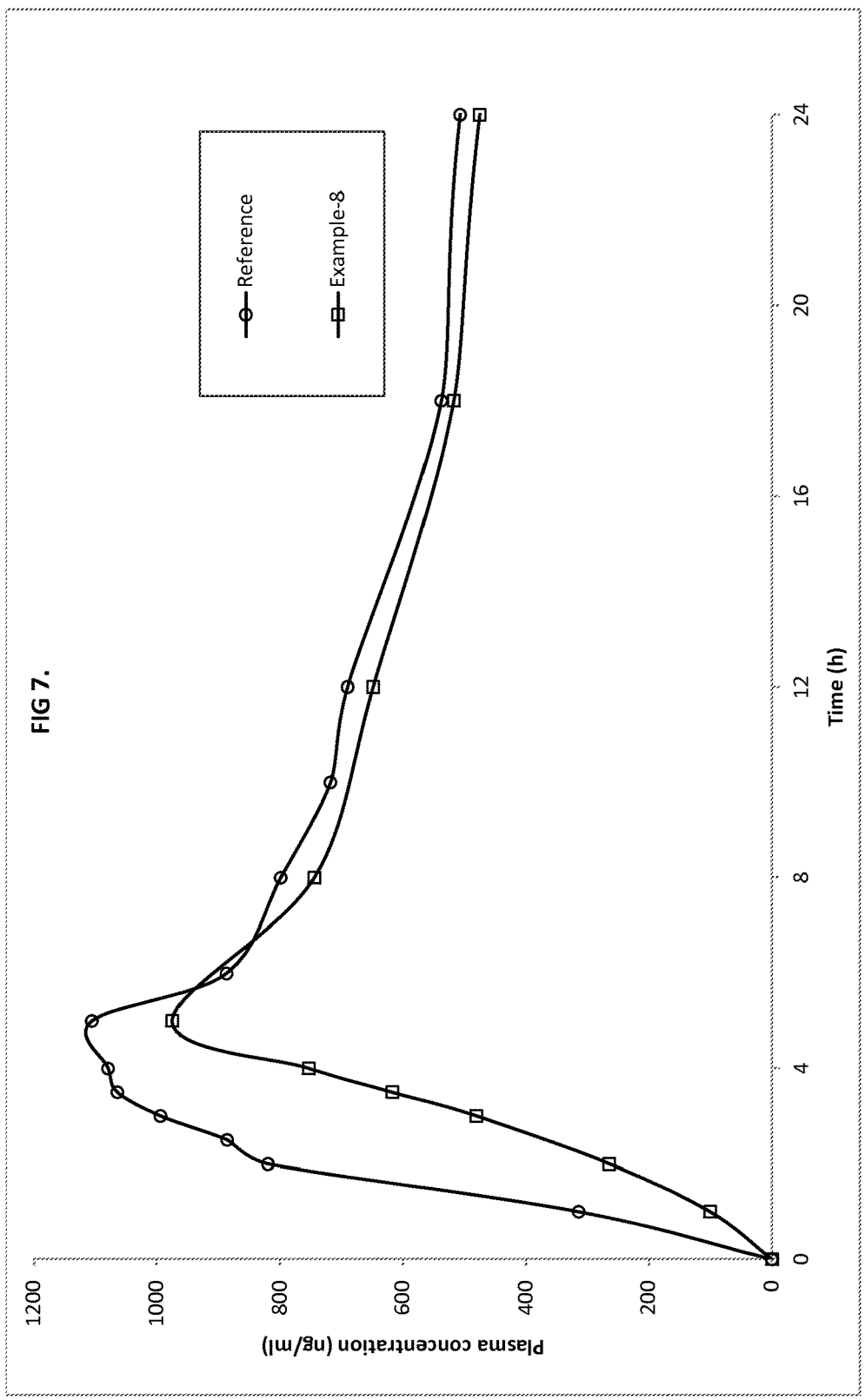
FIG. 7 represents the comparative in vivo pharmacokinetic profiles of controlled release pharmaceutical dosage form of doxycycline described in Example 8 and the reference product as measured in a single dose study.
Figure 8:
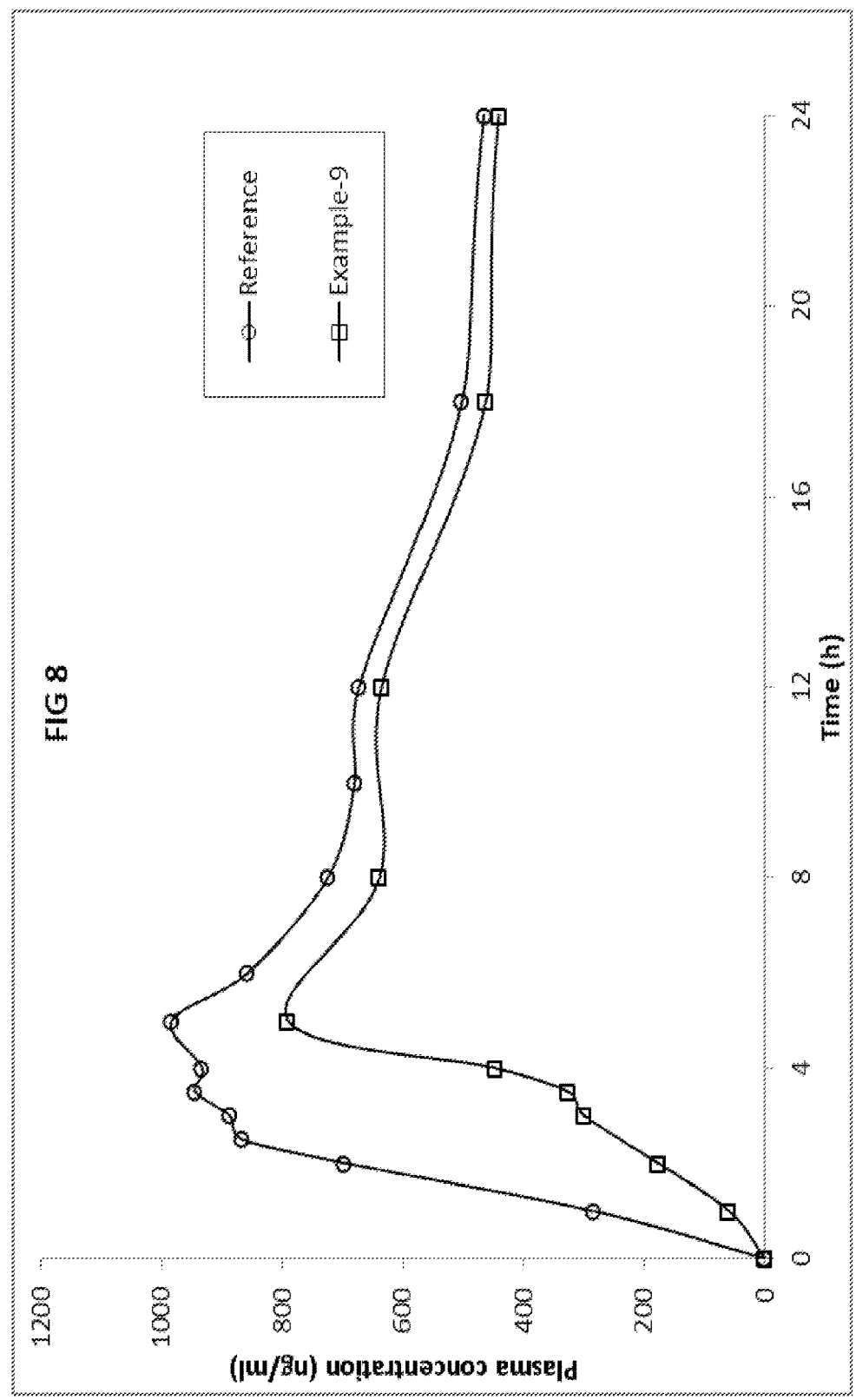
FIG. 8 represents the comparative in vivo pharmacokinetic profiles of controlled release pharmaceutical dosage form of doxycycline described in Example 9 and the reference product as measured in a single dose study.
Figure 9:
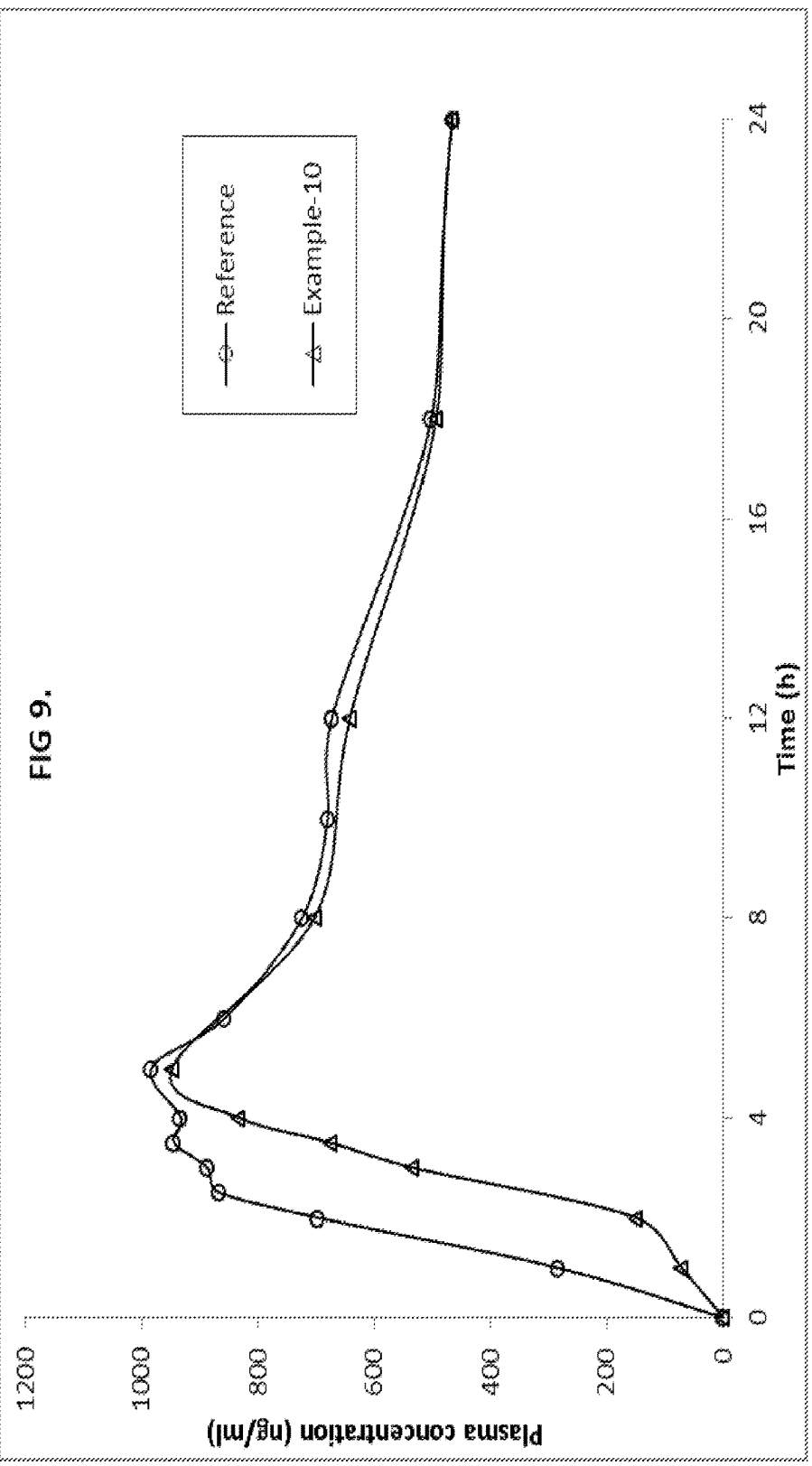
FIG. 9 represents the comparative in vivo pharmacokinetic profiles of controlled release pharmaceutical dosage form of doxycycline described in Example 10 and the reference product as measured in a single dose study.

Bioadhesion Testing:

Bioadhesion was determined by a tensiometric method. Advanced force gauge equipment (mfg. by Mecmesin, West Sussex, England) was used. Freshly excised sheep intestinal tissue was harvested and stored in Tyrode solution at 4° C. until it was used for the experiment. The tissue was cut into pieces (3×4 cm), mounted on a glass slide and tightened in place with a thread. A 0.5 ml volume of phosphate buffered saline (PBS) was placed on the tissue. Subsequently, one of tablets F1 through F6, was placed on tissue and another 0.5 ml PBS was placed on the tablet. A glass slide with a 10 g weight was placed on the tablet and it was allowed to hydrate for 10, 30, 60, 840 or 960 minutes. At the specified time interval, the hydrated tablet along with the slide was mounted on the stage of the bioadhesion apparatus. The probe was then lowered at a fixed speed of 0.2 mm/sec and the upper slide was attached to the hook of the probe by means of a thread. The peak detachment force was considered as the bioadhesive force and was measured as the force required to separate the tablet from the biological substrate. The peak detachment force is expressed in milliNewton (mN) and is presented in accompanying FIG. 3.

The peak detachment force was found to be above 1300 mN for formulations F1 to F5 and above 750 mN for F6 within the initial 10 mins of hydration. For each of F1 through F5, the peak detachment force was found to further increase beyond 1500 mN upon 60 minutes of hydration. For F6, the bioadhesive force increased to above 1100 mN after 60 minutes of hydration and was maintained at that level up to 960 minutes of hydration. For formulations F1, F2 & F5 the peak detachment force was maintained above 1500 mN at 960 mins. For F3 and F4, the peak detachment force decreased beyond 60 minutes of hydration but was still maintained above 500 mN at 960 mins.

Although this application has been described in detail above, it will be understood by one of ordinary skill in the art that various modifications can be made without departing from the spirit of the invention.

What is claimed is:

1. A method for treating acne, rosacea, or a combination thereof comprising administering to a patient in need thereof a controlled release doxycycline dosage form comprising an amount of immediate release doxycycline, wherein said doxycycline dosage form has a $t_{max}$ that is at least about 1.15 times greater than the $t_{max}$ of an immediate release doxycycline dosage form of equivalent strength.

2. The method of claim 1, wherein said doxycycline dosage form has a $t_{max}$ that is at least about 1.2 times greater than the $t_{max}$ of an immediate release doxycycline dosage form of equivalent strength.

3. The method of claim 1, wherein said doxycycline dosage form has a $t_{max}$ that is at least about 1.5 times greater than the $t_{max}$ of an immediate release doxycycline dosage form of equivalent strength.

4. The method of claim 1, wherein said doxycycline dosage form has a $t_{max}$ that is at least about 1.7 times greater than the $t_{max}$ of an immediate release doxycycline dosage form of equivalent strength.

5. A method for treating acne, rosacea, or a combination thereof comprising administering to a patient in need thereof a controlled release doxycycline pharmaceutical dosage form comprising an amount of immediate release doxycycline, wherein said controlled release doxycycline pharmaceutical dosage form has a mean $C_{max}$ that is at least about 70% that of an immediate release doxycycline dosage form of equivalent strength and has at least one of an $AUC_{0-48}h$ or an $AUC_{0-96}h$ that is at least about 85% of an immediate release doxycycline dosage form of equivalent strength, wherein the amount of immediate release doxycycline is contained in an immediate release doxycycline layer.

6. The method of claim 5, wherein the immediate release doxycycline layer is an immediate release doxycycline overcoat.

7. The method of claim 1, wherein the amount of immediate release doxycycline is contained in an immediate release doxycycline overcoat.

8. The method of claim 1, wherein the amount of immediate release doxycycline is contained in an immediate release doxycycline layer.

9. The method of claim 6, wherein the controlled release doxycycline pharmaceutical dosage form comprises:
a controlled release doxycycline layer, a swellable and/or floating layer, an expandable porous coating, and an immediate release doxycycline overcoat, or
a swellable controlled release doxycycline core, a permeable/expandable porous coating, and an immediate release doxycycline overcoat, or
a controlled release doxycycline layer, an inert swellable/bioadhesive layer, and an immediate release doxycycline overcoat.

10. The method of claim 6, wherein the controlled release doxycycline pharmaceutical dosage form comprises:
a controlled release doxycycline layer, a swellable and/or floating layer, an expandable porous coating, and an immediate release doxycycline overcoat, wherein the controlled release doxycycline layer includes a first amount of doxycycline and the immediate release doxycycline layer includes a second amount of doxycycline, wherein the first amount of doxycycline is from 5 to 15 weight % doxycycline based on the total weight of the dosage form and the second amount of doxycycline is from 0.5 to 3.2 weight % doxycycline based on the total weight of the dosage form, or
a swellable controlled release doxycycline core, a permeable/expandable porous coating, and an immediate release doxycycline overcoat, wherein the swellable controlled release doxycycline core comprises from 5 to 15 weight % doxycycline based on the total weight of the dosage form, and the immediate release doxycycline overcoat comprises from 0.5 to 3.2 weight % doxycycline based on the total weight of the dosage form, or
a controlled release doxycycline layer, an inert swellable/bioadhesive layer, and an immediate release doxycycline overcoat, wherein the controlled release doxycycline layer comprises from 5 to 15 weight % doxycycline based on the total weight of the dosage form, and the immediate release doxycycline overcoat comprises from 0.5 to 3.2 weight % doxycycline based on the total weight of the dosage form.

11. The method of claim 6, wherein the dosage form comprises a controlled release doxycycline layer, a swellable and/or floating layer, an expandable porous coating, and an immediate release doxycycline overcoat, wherein the controlled release doxycycline layer includes a first amount of doxycycline and the immediate release doxycycline layer includes a second amount of doxycycline, wherein the first amount of doxycycline is from 5 to 15 weight % doxycycline based on the total weight of the dosage form and the second amount of doxycycline is from 0.5 to 3.2 weight % doxycycline based on the total weight of the dosage form.

12. The method of claim 6, wherein the dosage form comprises a swellable controlled release doxycycline core, a permeable/expandable porous coating, and an immediate release doxycycline overcoat, wherein the swellable controlled release doxycycline core comprises from 5 to 15 weight % doxycycline based on the total weight of the dosage form, and the immediate release doxycycline overcoat comprises from 0.5 to 3.2 weight % doxycycline based on the total weight of the dosage form.

13. The method of claim 6, wherein the dosage form comprises a controlled release doxycycline layer, an inert swellable/bioadhesive layer, and an immediate release doxycycline overcoat, wherein the controlled release doxycycline layer comprises from 5 to 15 weight % doxycycline based on the total weight of the dosage form, and the immediate release doxycycline overcoat comprises from 0.5 to 3.2 weight % doxycycline based on the total weight of the dosage form.

14. The method of claim 6, wherein the controlled release doxycycline dosage form has at least one of an $AUC_{0-48}h$ or an $AUC_{0-96}h$ that is at least about 90% that of the immediate release doxycycline dosage form of equivalent strength.

15. The method of claim 6, wherein the controlled release doxycycline dosage form has at least one of an $AUC_{0-48}h$ or an $AUC_{0-96}h$ that is at least about 95% that of the immediate release doxycycline dosage form of equivalent strength.

16. The method of claim 6, wherein the controlled release doxycycline dosage form has at least one of an $AUC_{0-48}h$ or an $AUC_{0-96}h$ that is at least about 97% that of the immediate release doxycycline dosage form of equivalent strength.

17. The method of claim 6, wherein the controlled release doxycycline pharmaceutical dosage form has a mean $C_{max}$ that is at least about 80% that of an immediate release doxycycline dosage form of equivalent strength.

18. The method of claim 6, wherein the controlled release doxycycline pharmaceutical dosage form has a mean $C_{max}$ that is at least about 90% that of an immediate release doxycycline dosage form of equivalent strength.

19. The method of claim 6, wherein the controlled release doxycycline pharmaceutical dosage form has a mean $C_{max}$ that is at least about 95% that of an immediate release doxycycline dosage form of equivalent strength.

20. The method of claim 7, wherein the controlled release doxycycline pharmaceutical dosage form comprises:
a controlled release doxycycline layer, a swellable and/or floating layer, an expandable porous coating, and an immediate release doxycycline overcoat, wherein the controlled release doxycycline layer includes a first amount of doxycycline and the immediate release doxycycline layer includes a second amount of doxycycline, wherein the first amount of doxycycline is from 5 to 15 weight % doxycycline based on the total weight of the dosage form and the second amount of doxycycline is from 0.5 to 3.2 weight % doxycycline based on the total weight of the dosage form, or a swellable controlled release doxycycline core, a permeable/expandable porous coating, and an immediate release doxycycline overcoat, wherein the swellable controlled release doxycycline core comprises from 5 to 15 weight % doxycycline based on the total weight of the dosage form, and the immediate release doxycycline overcoat comprises from 0.5 to 3.2 weight % doxycycline based on the total weight of the dosage form, or a controlled release doxycycline layer, an inert swellable/bioadhesive layer, and an immediate release doxycycline overcoat, wherein the controlled release doxycycline layer comprises from 5 to 15 weight % doxycycline based on the total weight of the dosage form, and the immediate release doxycycline overcoat comprises from 0.5 to 3.2 weight % doxycycline based on the total weight of the dosage form.

* * * * *